(12) United States Patent
Maynard et al.

(10) Patent No.: US 10,201,613 B2
(45) Date of Patent: Feb. 12, 2019

(54) METHOD OF CREATING HYDROGELS THROUGH OXIME BOND FORMATION

(71) Applicant: THE REGENTS OF THE UNIVERSITY OF CALIFORNIA, Oakland, CA (US)

(72) Inventors: Heather D. Maynard, Los Angeles, CA (US); Tatiana Segura, Los Angeles, CA (US); Gregory Grover, Carlsbad, CA (US); Jonathan Lam, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/426,259

(22) PCT Filed: Aug. 20, 2013

(86) PCT No.: PCT/US2013/055769
§ 371 (c)(1),
(2) Date: Mar. 5, 2015

(87) PCT Pub. No.: WO2014/039245
PCT Pub. Date: Mar. 13, 2014

(65) Prior Publication Data
US 2015/0202305 A1 Jul. 23, 2015

Related U.S. Application Data

(60) Provisional application No. 61/697,988, filed on Sep. 7, 2012.

(51) Int. Cl.
| | |
|---|---|
| *A61K 47/42* | (2017.01) |
| *A61K 9/00* | (2006.01) |
| *A61K 9/06* | (2006.01) |
| *A61K 35/545* | (2015.01) |
| *C08G 65/48* | (2006.01) |
| *C08J 3/075* | (2006.01) |
| *C08J 3/24* | (2006.01) |
| *C08L 101/02* | (2006.01) |
| *C08L 101/06* | (2006.01) |
| *C08G 65/333* | (2006.01) |
| *C08G 65/337* | (2006.01) |

(52) U.S. Cl.
CPC ............ *A61K 47/42* (2013.01); *A61K 9/0024* (2013.01); *A61K 9/06* (2013.01); *A61K 35/545* (2013.01); *C08G 65/337* (2013.01); *C08G 65/33303* (2013.01); *C08G 65/33337* (2013.01); *C08G 65/48* (2013.01); *C08J 3/075* (2013.01); *C08J 3/246* (2013.01); *C08L 101/025* (2013.01); *C08L 101/06* (2013.01); *C08G 2650/30* (2013.01); *C08G 2650/44* (2013.01); *C08J 2300/104* (2013.01); *C08J 2300/106* (2013.01); *C08L 2203/02* (2013.01)

(58) Field of Classification Search
CPC ...... A61K 9/0024; A61K 9/06; A61K 35/545; A61K 47/42; C08G 65/33303; C08G 65/33337; C08G 65/337; C08G 65/48; C08G 2650/30; C08G 2650/44; C08J 3/075; C08J 3/246; C08J 2300/104; C08J 2300/106; C08L 101/06; C08L 101/025; C08L 2203/02
See application file for complete search history.

(56) References Cited

U.S. PATENT DOCUMENTS

| | | |
|---|---|---|
| 5,514,379 A | 5/1996 | Weissleder et al. |
| 6,846,923 B2 | 1/2005 | Wang et al. |
| 7,968,085 B2 | 6/2011 | Hersel et al. |
| 2002/0064546 A1* | 5/2002 | Harris ............... A61K 47/10 424/426 |

FOREIGN PATENT DOCUMENTS

WO 2009-108100 A1 9/2009

OTHER PUBLICATIONS

Ossipov, D.A., et al.; Macromolecules, 2008, p. 3971-3982.*
Roberts, M.C.; New In Situ Crosslinking Chemistries for Hydrogelation, 2008, p. i-149.*
Dirksen, A., et al.; Angewandte Chemie International Edition, 2006, p. 7581-7584.*
Jin, Y., et al., Biomacromolecules, 2011, p. 3460-3468 and Supporting Information, p. 1-10.*
Kalia, J., et al., Angew. Chem. Int. Ed., 2008, p. 7523-7526.*
Zhu, J., et al., Expert Rev. Med. Devices, 2012, p. 1-37.*
PCT International Search Report and Written Opinion, PCT/US2013/055769, dated Dec. 23, 2013.
Zacchinga, Marina et al., Multimeric, Multifunctional Derivatives of Poly(ehtylene glycol), Polymers, Jul. 1, 2011, vol. 3, No. 3, pp. 1076-1090.
Grover, Gregory et al., Biocompatible Hydrogels by Oxime Click Chemistry, Biomacromolecules, Oct. 8, 2012, vol. 13, No. 10, pp. 3013-3017.
Grover, Gregory et al., Oxime Cross-Linked Injectable Hydrogels for Catheter Delivery, Adv. Mater. 2013, 25, pp. 2937-2942.

* cited by examiner

*Primary Examiner* — Robert S Jones
(74) *Attorney, Agent, or Firm* — Quarles & Brady LLP

(57) ABSTRACT

A method of creating a hydrogel, comprising the step of condensing first and second functional groups, wherein the first group comprises a molecule or macromolecule of interest containing two or more hydroxylamine or aminooxy groups and the second group comprises a molecule or macromolecule of interest containing two or more aldehyde/ketone/other reactive oxo groups, under conditions such that a hydrogel forms.

22 Claims, 12 Drawing Sheets

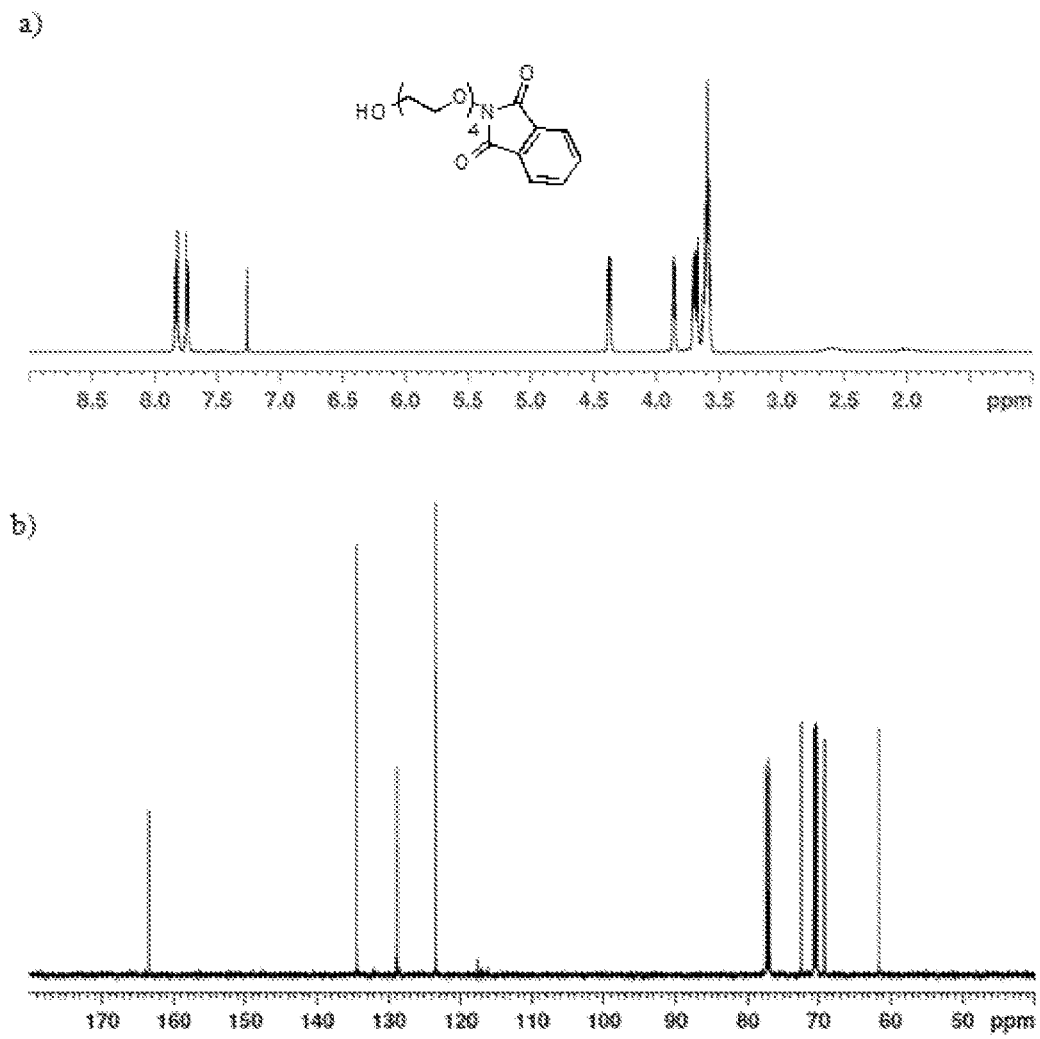
Figure 5 - A & B

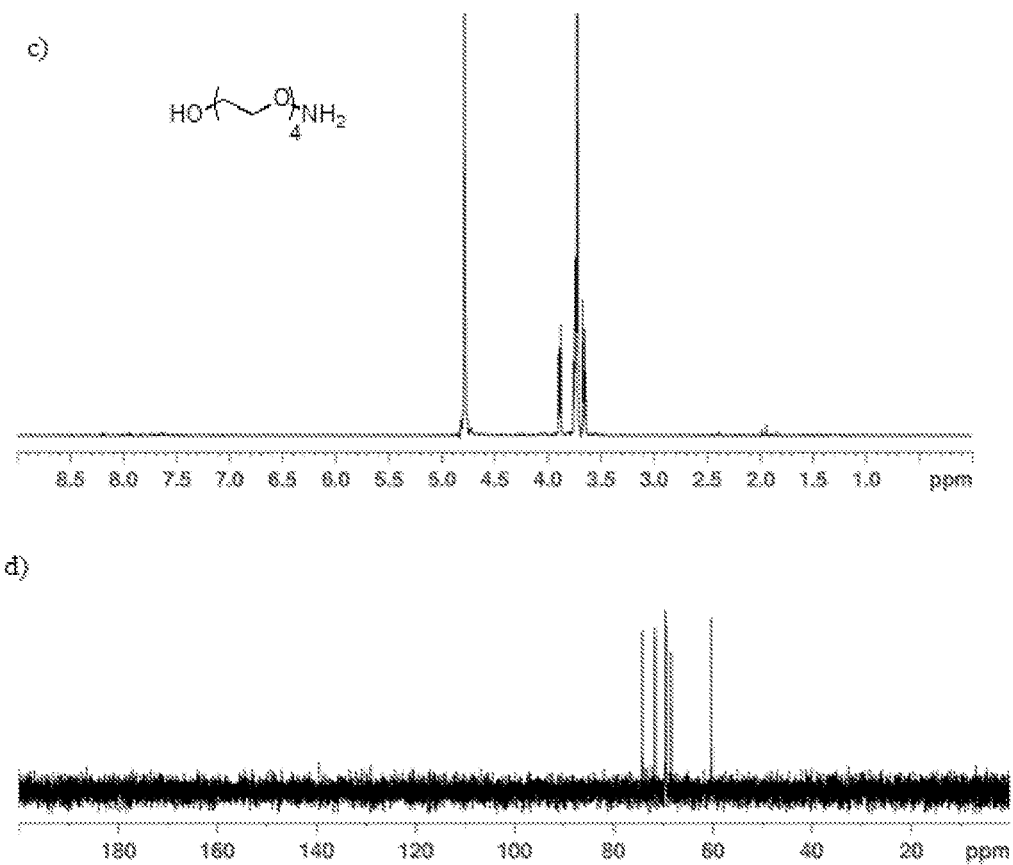
Figure 5 - C & D

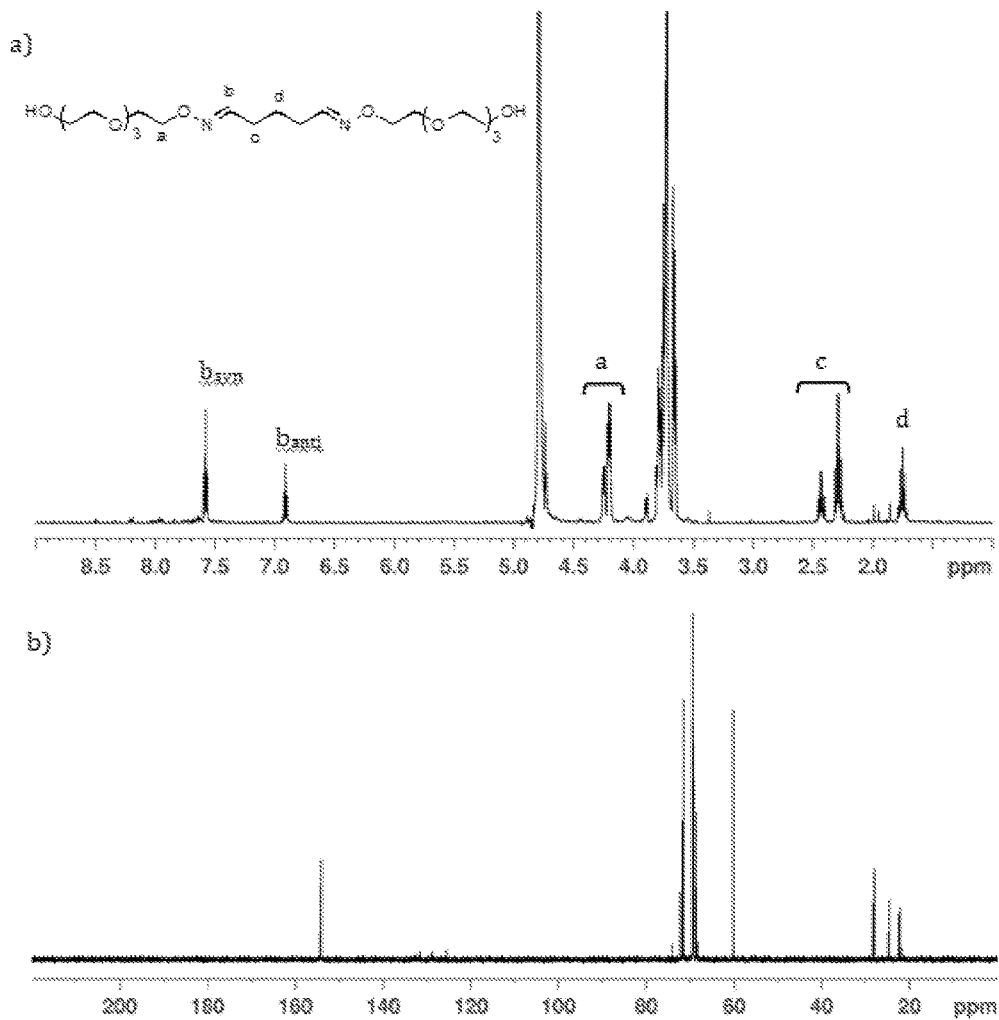
Figure 6 - A & B

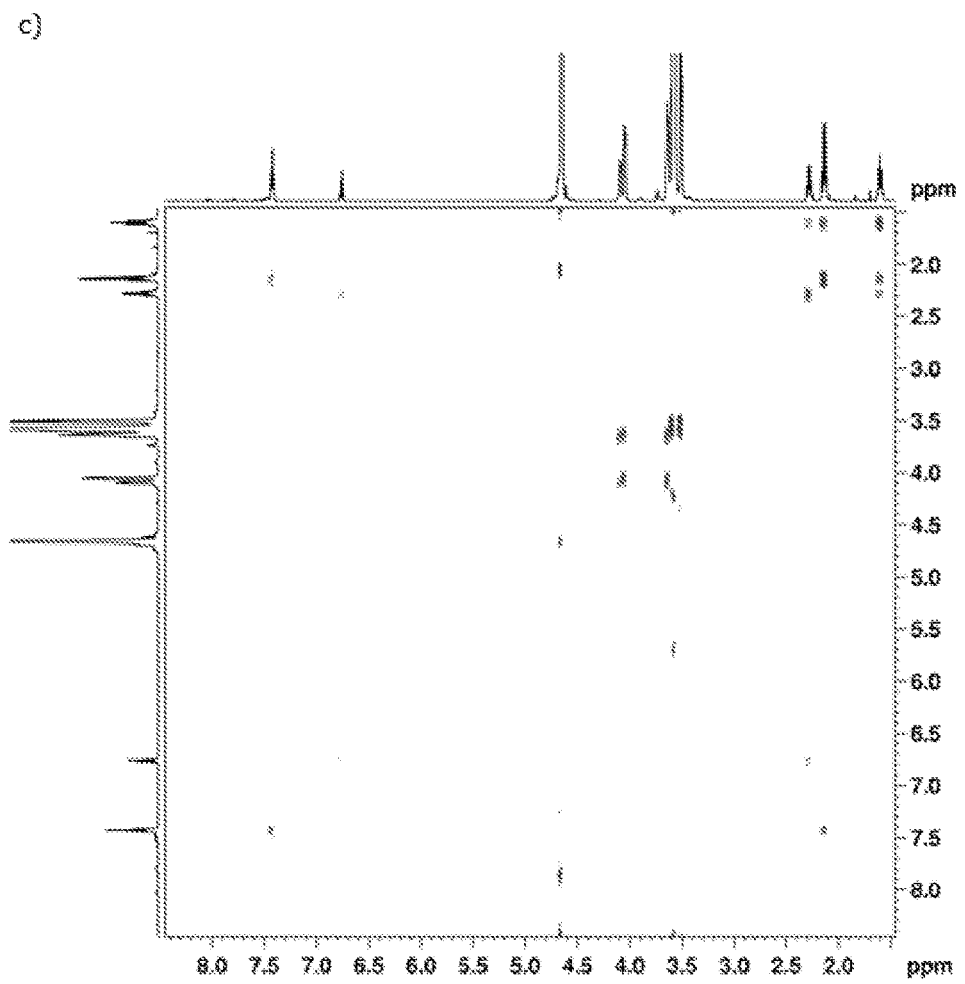
Figure 6 - C

METHOD OF CREATING HYDROGELS THROUGH OXIME BOND FORMATION

STATEMENT REGARDING FEDERALLY SPONSORED RESEARCH/DEVELOPMENT

This invention was made with government support of Grant Numbers CA137506 and GM067555, awarded by the National Institutes of Health. The government has certain rights in this invention.

CROSS-REFERENCE TO RELATED APPLICATIONS

This application represents the national stage entry of PCT International Application No. PCT/US2013/055769 filed Aug. 20, 2013, which claims benefit from U.S. Provisional Patent Application 61/697,988 filed Sep. 12, 2012, the disclosures of which are incorporated herein by reference in their entirety for all purposes.

FIELD OF THE INVENTION

Method of creating hydrogels through oxime bond formation is disclosed. Specifically, the method of creating hydrogels comprises the step of condensing first and second functional groups, wherein the first group comprises a molecule or macromolecule of interest containing two or more hydroxylamine or aminooxy groups and the second group comprises a molecule or macromolecule of interest containing two or more aldehyde/ketone/other reactive oxo group, under conditions such that a hydrogel forms.

BACKGROUND

Currently, a large number of methods have been utilized for chemically crosslinking hydrogels, including Michael addition reactions (e.g. Lutolf M P & Hubbell J A, 2003), radical crosslinking reactions (e.g. Hem D L & Hubbell J A (1998) Incorporation of adhesion peptides into nonadhesive hydrogels useful for tissue resurfacing. J Biomed Mater Res 39(2):266-276) and self assembly (e.g. Cellesi F, Weber W, Fussenegger M, Hubbell J A, & Tirelli N (2004) Towards a fully synthetic substitute of alginate: Optimization of a thermal gelation/chemical cross-linking scheme ("tandem" gelation) for the production of beads and liquid-core capsules. Biotechnology and Bioengineering 88(6):740-749). Specific chemistries utilized include thiol-ene, thiol-yne, Huisgens cycloaddition, Diels Alder reaction, and Native Chemical Ligation (Nimmo, C. M.; Shoichet, M. S. Bioconjug Chem 2011, 22, 2199-2209).

Many of these hydrogels have unacceptable limitations, such as the chemistry used for gelation reacting with the payload being encapsulated. For example, in the case of Michael-addition-crosslinked hydrogels, the crosslinker used is a di-cysteine-containing molecule that can act as a reducing agent for proteins. Thus, proteins incorporated in these hydrogels may have comprimised activity. In the case of radically crosslinked gels, the radicals can decrease the viability of cells through reactions with DNA and proteins. In other cases, such as the Huisgens cycloaddition, the addition of a toxic metal, such as copper, is required.

Furthermore, in some cases the starting materials can be unstable to storage. For example, thiols may oxidize or form disulfides.

Needed in the art is a hydrogel with improved stability and therapeutic properties.

SUMMARY OF THE INVENTION

In one aspect, the present invention relates to a method of creating a hydrogel, comprising the step of condensing first and second functional groups, wherein the first group comprises a molecule or macromolecule of interest containing two or more hydroxylamine or aminooxy groups and the second group comprises a molecule or macromolecule of interest containing two or more aldehyde/ketone/other reactive oxo groups, under conditions such that a hydrogel forms. In one embodiment, the molecules or macromolecules of interest are homopolymers or co-polymers having the general structures of

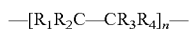

wherein $R_1$-$R_4$ are independently selected from hydrogen or a side chain comprising at least one carbon atom selected from the group consisting of -Alkyl, -Alkenyl, -Alkynyl, -Aryl, -Heteroaryl, and -Heterocyclyl.

In another embodiment, the molecules or macromolecules of interest are selected from the group consisting of polyethylene glycol, polyethylene glycol (PEG) derivative, polystyrene sulfonate, poly(styrene sulfonate-co-polyethylene glycol methacrylate), polypropylene oxide, polyethylene oxide, and poly(styrene sulfonate-co-polyethylene glycol acrylate).

In another embodiment, the molecule or macromolecule of interest in the second group comprises two or more groups of $R_1CO$-L-$COR_2$, wherein $R_1$ and $R_2$ are independently selected from the group consisting of H, Cl, Br, I, -Alkyl, -Alkenyl, -Alkynyl, -Aryl, -Heteroaryl, -Heterocyclyl, OR3, SR4, NR5, and biomolecules and L is a linker molecule, and wherein $R_3$, $R_4$ and $R_5$ are independently selected from the group consisting of H, Cl, Br, I, -Alkyl, -Alkenyl, -Alkynyl, -Aryl, -Heteroaryl and -Heterocyclyl, and wherein L is selected from the group consisting of -Alkyl-, -Alkenyl-, Alkynyl-, -Aryl-, -Heteroaryl-, -Heterocyclyl-, and —$(CH_2CH_2O)n$-, wherein n=0-1000.

In another aspect, the present invention relates to a method of creating a hydrogel, comprising the step of condensing functional groups, wherein the functional groups comprise a molecule or macromolecule of interest containing two or more hydroxylamine or aminooxy groups and two or more aldehyde/ketone/other reactive oxo groups, under conditions such that a hydrogel forms.

In another aspect, the present invention relates to a hydrogel comprising a condensation product wherein the condensation product forms from condensing first and second functional groups, and wherein the first group comprises a molecule or macromolecule of interest containing two or more hydroxylamine or aminooxy groups and the second group comprises a molecule or macromolecule of interest containing two or more aldehyde/ketone/other reactive oxo groups.

In another aspect, the present invention relates to a method for storing and delivering cells comprising the steps of a) mixing cells with either first or second functional groups, wherein the first group comprises a molecule or macromolecule of interest containing two or more hydroxylamine or aminooxy groups and the second group comprises a molecule or macromolecule of interest containing two or more aldehyde/ketone/other reactive oxo groups; and b) condensing the first and the second functional groups to form a hydrogel, wherein the cells are stored in the hydrogels.

In another aspect, the present invention relates to a method for controlling release of a polypeptide from a hydrogel into an environment, the method comprising the step of a) forming a hydrogel according to any of the methods as discussed above, wherein the molecule or macromolecule of interest in the hydrogel further comprises a polypeptide having a amino acid sequence and wherein a chemical bond forms between the polypeptide and the molecule or macromolecule of interest in the hydrogel; b) placing the hydrogel in an environment, and adding an enzyme into the environment; and c) allowing the enzyme to cleave the chemical bond between the polypeptide and the molecule or macromolecule of interest in the hydrogel and releasing the polypeptide into the environment.

BRIEF DESCRIPTION OF THE DRAWINGS

FIGS. 2A and 2B show that altering polymer percentage while keeping the crosslinking ratio constant (r=1.0) can significantly change the mechanical properties of the hydrogel. FIGS. 2C and 2D show that, likewise, changing the crosslinking ratio while keeping the polymer percentage constant (PEG: 3%) can drastically change the storage/loss modulus.

FIG. 3A shows that making the solution more acidic can increase the rate of gelation whereas a more basic solution slows down the gelation kinetics for 3 wt % AO-PEG (r=1). Increasing the storage modulus by adjusting the PEG percentage (PEG=3, 5, 7% from left to right) while keeping the crosslinking ratio constant at r=1 (open circles) decreases the water content (B) and increases the swell ratios (C). Increasing the storage modulus by changing the r ratio (r=0.7, 0.8, 1.0 from left to right) while keeping the PEG percentage constant at 3 wt % (closed triangles) decreases the water content as shown in FIG. 3B and decreases the swelling ratio as shown in FIG. 3C. Data is displayed as the average and standard deviation of three independent experiments.

FIG. 4D shows that cells seeded on top of the hydrogel spread after one day, whereas cells encapsulated inside did not spread at (FIG. 4E) day 1, (FIG. 4F) day 4, (FIG. 4G) and day 7. FIG. 4H shows that MTT assay demonstrating an increased reduction over time, which indicates that cells are proliferating inside the hydrogel. FIG. 4 shows the SEM image of hydrogel structure.

FIG. 5 is a set of images showing NMR spectra of some of the the starting materials. FIG. 5a shows $^1$H NMR and FIG. 5b shows $^{13}$C NMR spectra of N-hydroxyphthalimide tetra(ethylene glycol) in CDCl$_3$. FIG. 5c shows $^1$H NMR and FIG. 5d shows $^{13}$C NMR spectra of O-hydroxylamine tetra(ethylene glycol) in D$_2$O.

FIG. 6 is a set of images showing NMR and 2D NMR spectra of some of the starting materials. FIG. 6a shows $^1$H NMR, FIG. 6b shows $^{13}$C NMR and FIG. 6c shows COSY spectra of O-hydroxylamine tetra(ethylene glycol) and glutaraldehyde in D$_2$O.

FIG. 9 also discloses a hydrogel after formation that includes RGD peptide.

BRIEF DESCRIPTION OF THE PRESENT INVENTION

In General

Figure 1:
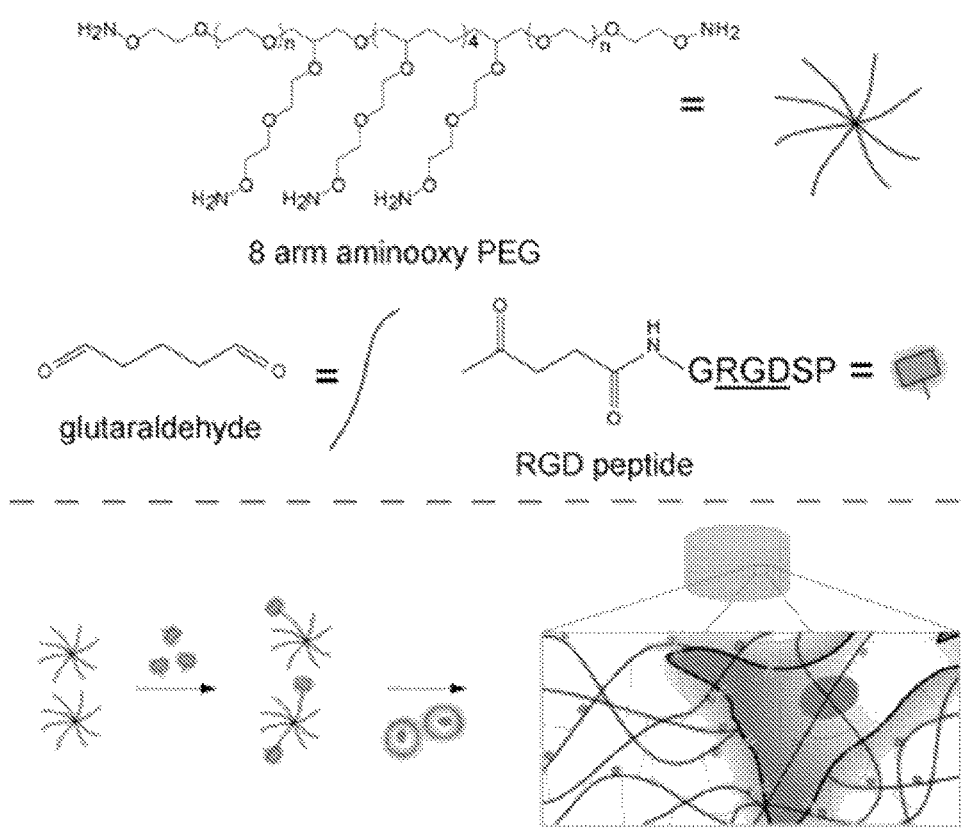
FIG. 1 is schemetic diagrams showing synthesis and encapsulation of MSCs within RGD-functionalized oxime-cross-linked PEG hydrogels. Note that glutaraldehyde is generally a mixture of species and thus the structure shown is idealized.

"Aliphatic" refers to aliphatic carbon chains including alkyl, alkenyl and alkynyl groups as further defined herein.

"Alkyl", alone or in combination, refers to an aliphatic carbon chain which may be straight chained or branched and preferably have from 1 to 10 carbon atoms or more preferably 1 to 6 carbon atoms. Examples of such alkyl groups include methyl, ethyl, n-propyl, iso-propyl, n-butyl, iso-butyl, n-hexyl, and the like. The alkyl group may also exist in the form of a divalent radical known as an "Alkylene" group.

"Alkenyl", alone or in combination, refers to an unsaturated aliphatic carbon chain which may be straight chained or branched and preferably have from 2 to 10 carbon atoms and more preferably 2 to 6 carbon atoms and have at least 1 and preferably from 1-2, carbon to carbon, double bonds. Examples include ethenyl (—CH═CH$_2$), n-propenyl (—CH$_2$CH═CH$_2$), iso-propenyl (—C(CH3)═CH$_2$), but-2-enyl (—CH$_2$CH═CHCH3), and the like. The alkenyl group may also exist in the form of a divalent radical known as an "Alkenylene" group.

"Alkynyl", alone or in combination, refers to alkynyl groups preferably having from 2 to 10 carbon atoms and more preferably 2 to 6 carbon atoms and having at least 1, and preferably from 1-2, carbon to carbon, triple bonds. Examples of alkynyl groups include ethynyl (—C≡CH), propargyl (CH$_2$C≡CH), pent-2-ynyl (—CH$_2$C≡CCH$_2$—CH3), and the like. The alkynyl group may also exist in the form of a divalent radical known as an "Alkynylene" group.

"Aryl", alone or in combination, refers to an unsaturated aromatic carbocyclic group having a single ring (e.g., phenyl) or multiple condensed rings (e.g., naphthyl or anthryl), preferably having from 6 to 14 carbon atoms, preferably 6 carbon atoms. Examples of aryl groups include phenyl, naphthyl, and the like. The aryl group may also exist in the form of a divalent radical known as an "Arylene" group.

"Heteroaryl", alone or in combination, refers to a monovalent aromatic heterocyclic group which fulfils the Hückel criteria for aromaticity (i.e., contains 4n+2 π electrons, is planar and conjugated) and preferably has from 2 to 10 carbon atoms and 1 to 4 heteroatoms selected from oxygen, nitrogen, selenium, and sulfur within the ring (and includes oxides of sulfur, selenium, and nitrogen). Such heteroaryl groups can have a single ring (e.g., pyridyl, pyrrolyl, or N-oxides thereof, or furyl) or multiple condensed rings (e.g., indolizinyl, benzoimidazolyl, coumarinyl, quinolinyl, isoquinolinyl, or benzothienyl). Preferably heteroaryl is a 5-membered or 6-membered ring.

"Heterocyclyl", alone or in combination, refers to a monovalent saturated or unsaturated group having a single ring or multiple condensed rings, preferably from 1 to 8 carbon atoms and from 1 to 4 heteroatoms selected from nitrogen, sulfur, oxygen, selenium, and phosphorous within the ring. Preferably heterocyclyl is a 5-membered or 6-membered ring. Examples of heterocyclyl and heteroaryl groups include, but are not limited to, oxazole, pyrrole, imidazole, imidazoline, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7 tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, benzo[1,3]dioxole, and the like. Heterocyclyl rings can optionally also be fused to aryl rings, such that the definition includes bicyclic structures. Typically such fused heterocyclyl groups share one bond with an optionally substituted benzene ring. Examples of benzo-fused heterocyclyl groups include, but are not limited to, benzo[1,3]dioxole, benzimidazolidinone, tetrahydroquinoline, and methylenedioxybenzene ring structures. Binding to the heterocycle can be at the position of an heteroatom or via a carbon atom of the heterocycle, or, for benzo-fused derivatives, via an heteroatom and a carbon atom or of the benzene ring.

Examples of heterocyclyl and heteroaryl groups include, but are not limited to, oxazole, pyrrole, imidazole, imidazoline, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7 tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, benzo[1,3]dioxole, and the like. Heterocyclyl rings can optionally also be fused to aryl rings, such that the definition includes bicyclic structures. Typically such fused heterocyclyl groups share one bond with an optionally substituted benzene ring. Examples of benzo-fused heterocyclyl groups include, but are not limited to, benzo[1,3]dioxole, benzimidazolidinone, tetrahydroquinoline, and methylenedioxybenzene ring structures. Binding to the heterocycle can be at the position of an heteroatom or via a carbon atom of the heterocycle, or, for benzo-fused derivatives, via an heteroatom and a carbon atom or of the benzene ring.

"Cycloaliphatic" includes $C_3$-$C_8$ cycloalkyl and cycloalkene and heterocyclic variations thereof, as further described herein.

"Cycloalkyl", alone or in combination, refers to cyclic alkyl groups having a single cyclic ring or multiple condensed rings, preferably incorporating 3 to 8 carbon atoms. Such cycloalkyl groups include, by way of example, single ring structures such as cyclopropyl, cyclobutyl, cyclopentyl, cyclohexyl, cycloheptyl, cyclooctyl, and the like, or multiple ring structures such as adamantanyl, and the like.

"Cycloalkenyl", alone or in combination, refers to cyclic alkenyl groups having a single cyclic ring and at least one point of internal unsaturation, preferably incorporating 4 to 8 carbon atoms. Examples of suitable cycloalkenyl groups include, for instance, cyclobut-2-enyl, cyclopent-3-enyl, cyclohex-4-enyl, cyclooct-3-enyl, and the like.

"Ester", alone or in combination, refers to a group comprising a carboxylate of general formula —C(=O)O— including, though not limited to alkyl esters, aryl esters and combinations thereof such as alkyl-C(=O)O-aryl groups.

"Ether", alone or in combination, refers to an aliphatic or cycloaliphatic carbon chain interrupted by at least one oxygen atom. Examples include, though are not limited to, methoxy, ethoxy, propoxy, butoxy, pentoxy, furanyl and pyranyl groups.

"Halo" or "halogen", alone or in combination, refers to fluoro, chloro, bromo, and iodo.

"Aminooxy", alone or in combination, refers to the group —ONH$_2$. In the present invention, the term "aminooxy" and the "hydroxylamine" may be used interchangably.

The term "oxo" refers to the group C=O.

The term "acyl" or "aldehyde" refers to the group —C(=O)H.

The term "substituted acyl" or "ketone" refers to an acyl group having a hydrogen replaced with, for example a $C_{1-6}$alkyl group ("$C_{1-6}$alkylacyl" or "alkylketone" or "ketoalkyl"), an aryl group ("arylketone"), an aralkyl group ("aralkylketone) and so on. $C_{1-3}$alkylacyl groups are preferred.

The term "amido" or "amide" refers to the group —C(O)NH$_2$.

The term "aminoacyl" refers to the group —NHC(O)H.

The term "substituted amido" or "substituted amide" refers to an amido group having a hydrogen replaced with, for example a $C_{1-6}$alkyl group ("$C_{1-6}$alkylamido" or "$C_{1-6}$alkylamide"), an aryl ("arylamido"), aralkyl group ("aralkylamido") and so on. $C_{1-3}$alkylamide groups are preferred, such as for example, methylamide (—C(O)NHMe), ethylamide (—C(O)NHEt) and propylamide (—C(O)NHPr) and includes reverse amides thereof (e.g., —NHMeC(O)—, —NHEtC(O)— and —NHPrC(O)—).

The term "disubstituted amido" or "disubstituted amide" refers to an amido group having the two hydrogens replaced with, for example a $C_{1-6}$alkyl group ("di($C_{1-6}$alkyl)amido" or "di($C_{1-6}$alkyl)amide"), an aralkyl and alkyl group ("alkyl (aralkyl)amido") and so on. Di($C_{1-3}$alkyl)amide groups are preferred, such as for example, dimethylamide (—C(O)NMe$_2$), diethylamide (—C(O)NEt$_2$) and dipropylamide ((—C(O)NPr$_2$) and variations thereof (e.g., —C(O)N(Me)Et and so on) and includes reverse amides thereof.

"Amino acids", alone or in combination, include common amino acids such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

"Thio", alone or in combination, refers to groups H—S—, alkyl-S—, cycloalkyl-S—, aryl-S—, heteroaryl-S—, and heterocyclyl-S—, where alkyl, cycloalkyl, aryl, heteroaryl, and heterocyclyl are as described herein.

"Thioalkyl", alone or in combination, refers to —S-alkyl, where alkyl is a described herein.

"Thioacyl", alone or in combination, refers to groups H—C(S)—, alkyl-C(S)—, cycloalkyl-C(S)—, aryl-C(S)—, heteroaryl-C(S)—, and heterocyclyl-C(S)—, where alkyl, cycloalkyl, aryl, heteroaryl, and heterocyclyl are as described herein.

"Sulfinyl", alone or in combination, refers to groups H—S(O)—, alkyl-S(O)—, cycloalkyl-S(O)—, aryl-S(O)—, heteroaryl-S(O)—, and heterocyclyl-S(O)—, where alkyl, cycloalkyl, aryl, heteroaryl, and heterocyclyl are as described herein.

"Sulfonyl", alone or in combination, refers to groups H—S(O)2-, alkyl-S(O)2-, cycloalkyl-S(O)2-, aryl-S(O)2-, heteroaryl-S(O)2-, and heterocyclyl-S(O)2-, where alkyl, cycloalkyl, aryl, heteroaryl, and heterocyclyl are as described herein.

The term "protein" used herein refers to any compound of two or more individual amino acids (whether or not naturally occurring) linked via peptide bonds, as occur when the carboxyl carbon atom of the carboxylic acid group bonded to the α-carbon of one amino acid (or amino acid residue) becomes covalently bound to the amino nitrogen atom of the amino group bonded to the a-carbon of an adjacent amino acid. These peptide bond linkages, and the atoms comprising them (i.e., α-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide." The examplary peptides may include integrin binding peptides and MMP cleavable peptides. Similarly, protein fragments, analogs, derivatives, and variants are may be referred to herein as "proteins," and shall be deemed to be a "protein" unless otherwise indicated. The term "fragment" of a protein refers to a polypeptide comprising fewer than all of the amino acid residues of the protein. As may be appreciated, a "fragment" of a protein may be a form of the protein truncated at the amino terminus, the carboxyl terminus, and/or internally (such as by natural splicing), and may also be variant and/or derivative. A "domain" of a protein is also a fragment, and comprises the amino acid residues of the protein required to confer biochemical activity corresponding to naturally occurring protein. The term "protein" used herein also include "protein conjugate" which refers to a compound complex comprising a "protein" which is interlinked to one another molecule or subject. The term "complex" is used herein to mean those compounds comprising at least two components. The protein may be naturally occurring and isolated from its source. The protein may be produced using DNA recombination or mutation techniques. The protein may be produced in vivo in a whole animal, or in a eukaryotic or prokaryotic cell; alternatively, the protein may be generated using an in vitro method such as cell-free in vitro translation, e.g., using E. coli lysate, wheat germ extract, or rabbit reticulocyte. Cell free in vitro translation methods can be employed following in vitro transcription, e.g., following phage or ribosome display.

Examples of proteins include, without limitation, Lysozyme, Adenosine deaminase, L-Asparaginase, Mammalian urate oxidase, Interferons, Anti-TNF α Fab, granulocyte colony stimulated factor (G-CSF), Continuous erythropoietin receptor activator, hGH antagonist B2036, Insulin, Insulin human inhalation, Insulin aspart, Insulin glulisine, Insulin lispro, Isophane insulin, Insulin detemir, Insulin glargine, Insulin zinc extended, Pramlintide acetate, Growth hormone (GH), Somatotropin, Mecasermin, Mecasermin rinfabate, Factor VIII. Factor IX, Antithrombin III (AT-iii), fibroblast growth factor (FGF), basic fibroblast growth factor (bFGF), vascular endothelial growth factor (VEGF), platelet derived growth factor (PDGF), Protein C concentrate, β-Gluco-cerebrosidase, Alglucosidase-α, Laronidase (α-L-iduronidase), Idursulphase (iduronate-2-sulphatase), Galsulphase, Agalsidase-β (human α-galactosidase A), α-1-Proteinase inhibitor, Lactase, Pancreatic enzymes, lipase, amylase, protease, Adenosine deaminase, Pooled immunoglobulins, Human albumin, Erythropoietin, Epoetin-α, Darbepoetin-α, Sargramostim (granulocytemacrophage colony stimulating factor; GM-CSF), Oprelvekin (interleukin11; IL11) Human follicle-stimulating hormone (FSH), Human chorionic gonadotropin (HCG), Lutropin-α, Type I alpha-interferon, interferon alfacon 1, consensus interferon, Aldesleukin (interleukin 2 (IL2), epidermal thymocyte activating factor (ETAF), Alteolase (tissue plasminogen activator: tPA), Reteplase (deletion mutein of tPA), Tenecteplase, Urokinase, Factor VIa, Drotrecogin-α (activated protein C), Salmon calcitonin, Teriparatide (human parathyroid hormone residues 1-34), Exenatide, Octreotide, Dibotermin-α (recombinant human bone morphogenic protein 2; rhBMP2), Recombinant human bone morphogenic protein 7 (rhBMP7), Histrelin acetate (gonadotropin releasing hormone; GnrH), Palifermin (keratinocyte growth factor; KGF), Becaplermin (platelet-derived growth factor; PDGF), Trypsin, Nesiritide, Botulinum toxin type A, Botulinum toxin type B, Collages, Collagenase, Human deoxyribonuclease I, dornase-α, Hyaluronidase (bovine, ovine), Hyaluronidase (recombinant human), Papain, L-Asparaginase, Rasburicase, Lepirudin, Bivalirudin, Streptokinase, Anistreplase (anisoylated plasminogen streptokinase activator complex; APSAC), Bevacizumab, Cetuximab, Panitumumab, Alemtuzumab, Rituximab, Trastuzumab, Abatacept Anakinra, Adalimumab, Etanercept, Infliximab, Alefacept, Efalizumab, Natalizumab, Eculizumab, Antithymocyte globulin (rabbit), Basiliximab, Daclizumab, Muromonab-CD3, Omalizumab, Palivizumab, Enfuvirtide, Abciximab, Crotalidae polyvalent immune Fab (ovine), Digoxin immune serum Fab (ovine), Ranibizumab, Denileukin diftitox, Ibritumomab tiuxetan, Gemtuzumab ozogamicin, Tositumomab, and itositumomab.

A denatured protein can be fully denatured, or partially denatured or renatured such that the protein is in non-native form as unfolded protein and/or partially folded refolding intermediate(s). An aqueous solution or dried sample comprising denatured protein may contain one or more of these forms. A native protein is in a folded, functional conformation. Some protein may also be present in aqueous solution, or in a dried sample, in the form of contaminating aggregates and/or inclusion bodies.

The term "antibody" or "antibody molecule" as used herein refers to immunoglobulin molecules or other molecules which comprise an antigen binding domain. The term "antibody" or "antibody molecule" as used herein is thus intended to include whole antibodies (e.g., IgG, IgA, IgE, IgM, or IgD), monoclonal antibodies, polyclonal antibodies, and chimeric antibodies.

The term "antibody" also includes "antibody fragments" or "antibody-derived fragments" which comprise an antigen binding domain are also included. The term "antibody fragment" as used herein is intended to include any appropriate antibody fragment that displays antigen binding function, for example, Fab, Fab', F(ab')2, scFv, Fv, dsFv, ds-scFv, Fd, dAbs, TandAbs dimers, mini bodies, monobodies, diabodies, and multimers thereof and bispecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art.

The antibodies or antibody fragments can be produced naturally or can be wholly or partially synthetically produced. Thus the antibody may be from any appropriate source, for example recombinant sources and/or produced in transgenic animals or transgenic plants. Thus, the antibody molecules can be produced in vitro or in vivo. Preferably the antibody or antibody fragment comprises an antibody light chain variable region ($V_L$) and an antibody heavy chain variable region ($V_H$) which generally comprise the antigen binding site. The antibody or antibody fragment can comprises all or a portion of a heavy chain constant region, such as an IgG1, IgG2, IgG3, IgG4, IgA1, IgA2, IgE, IgM or IgD constant region. Preferably, the heavy chain constant region is an IgG1 heavy chain constant region. Furthermore, the antibody or antibody fragment can comprise all or a portion of a kappa light chain constant region or a lambda light chain constant region. All or part of such constant regions may be produced naturally or may be wholly or partially synthetic. Appropriate sequences for such constant regions are well known and documented in the art.

The term "fragment" as used herein refers to fragments of biological relevance (functional fragment), e.g., fragments which can contribute to or enable antigen binding, e.g., form part or all of the antigen binding site, or can contribute to the inhibition or reduction in function of the antigen or can contribute to the prevention of the antigen interacting with its natural ligands. Fragments thus comprise a heavy chain variable region ($V_H$ domain) and/or a light chain variable region ($V_L$ domain) of the antibodies of the invention. Fragments may also comprise one or more of the heavy chain complementarity determining regions (CDRs) of the antibodies or of the $V_H$ domains, or one or more of the light chain complementarity determining regions (CDRs) of the antibodies, or of the $V_L$ domains.

The term "hydrogel", as used herein, refers to a network of polymer chains with great water absorbance capacity, meaning that when placed in an aqueous environment the polymer chain network can absorb water and increase in volume through the absorption and retention of water in the polymeric mesh. Hydrogels may generally be hydrophilic. Sometimes a hydrogel may be found as a colloidal gel in which water is the dispersion medium. Hydrogels may be highly absorbent (they can contain over 99.9% water) natural or synthetic polymers. Hydrogels may also possess a degree of flexibility very similar to natural tissue, due to their significant water content. Common ingredients for hydrogels may include any suitable synthetic polymers, such as polyethylene glycol, polyethylene glycol derivative, polystyrene sulfonate and poly(styrene sulfonate-co-polyethylene glycol methacrylate) and poly(styrene sulfonate-co-polyethylene glycol acrylate), polyvinyl alcohol, sodium polyacrylate, acrylate polymers and copolymers with an abundance of hydrophilic groups. Common ingredients for hydrogels may also include any suitable natural materials such as agarose, methylcellulose, hyaluronan, and any other naturally derived polymers. In one embodiment, hydrogels in the present invention may be made of a polymer of polyethylene glycol, polyethylene glycol derivative, polystyrene sulfonate, poly(styrene sulfonate-co-polyethylene glycol methacrylate), poly(styrene sulfonate-co-polyethylene glycol acrylate), or a copolymer of any of the combinations of these polymers. In one specific embodiment, hydrogels in the present invention may be made of a polymer or a copolymer of polyethylene glycol or polyethylene glycol derivative.

The term "polyethylene glycol (PEG) derivative", as used herein, refers to any compound having a chemical structure including at least one polyethylene glycol group. Preferably, a PEG derivative may have at least two PEG groups. Each of PEG group in the PEG derivatives may further comprise functional groups. Any functional groups may be suitable for PEG derivatives in the present invention. Preferably, a PEG derivative in the present invention may comprise functional groups such as aminooxy groups or aldehyde/ketone/other oxo groups. More preferably, a PEG derivative in the present invention may comprise at least two aminooxy groups or aldehyde/ketone/other oxo groups.

The term "bio-degradable" or "degradable", as used herein, refers to the chemical dissolution of a substance by enzymes, bacteria or any other biological means. Generally, an enzyme may dissolute a substance by cleaving the chemical bonds in the substance. For example, the ability of an enzyme for cleaving chemical bonds in a peptide may be specific for the peptide sequence. In one embodiment of the present invention, a method for controlling release of a biomolecule may be designed by linking a hydrogel with the biomolecule through a peptide sequence specific for an enzyme.

The term "bio-compatible" or "bio-compatibility", as used herein, refers to an ability of certain substances to be in contact with a living system without producing an adverse effect. Bio-compatibility may also refer to the ability of a substance to perform with an appropriate host response in a specific application or the quality of a substance not having toxic or injurious effects on biological systems. Specifically, bio-compatibility may refer to comparison of the tissue response produced through the close association of the implanted candidate material to its implant site within the host animal to that tissue response recognised and established as suitable with control materials. In some embodiments, bio-compatibility may refer to the ability of a biomaterial to perform its desired function with respect to a medical therapy, without eliciting any undesirable local or systemic effects in the recipient or beneficiary of that therapy, but generating the most appropriate beneficial cellular or tissue response in that specific situation, and optimising the clinically relevant performance of that therapy or the capability of a prosthesis implanted in the body to exist in harmony with tissue without causing deleterious changes.

The term "cellular components", as used herein, refers to substances or biomolecules related to cell.

The present invention provides a method of making a hydrogel that relys on oxime bond formation between molecules. In some embodiments, the resulting hydrogels can be loaded with biological cues/therapeutics. The hydrogel can also be used to encapsulate cells.

Hydrogels are well-established materials for drug delivery and tissue engineering applications. These materials afford the ability to deliver therapeutics, act as scaffolds for tissue engineering, and provide cell encapsulation/delivery. These applications are possible because hydrogels are three dimensional networks which are highly hydrated and therefore are able to resemble biological tissue. These hydrolgel materials are also insoluble due to either physical crosslinks or chain entanglement yet can be made to dissolve given the correct biological cues such as enzymes. The method and extent of crosslinking is an important aspect that largely determines the mechanical properties, the biocompatibility, cell encapsulation/delivery and drug loading properties of the hydrogel.

The present invention generally relates to the chemistry used to form the gel and our discovery that hydroxylamine functionalized molecules and macromolecules and ketone/aldehyde functionalized molecules and macromolecules of interest can be loaded with biological cues/therapeutics and used to encapsulate cells via a hydrogel created through oxime bond formation without cytotoxicity to encapsulated cells. Oxime formation involves the reaction of an oxo group such as an aldehyde, ketone, or oxoamide or a nitrile with a hydroxylamine functionality, where the oxygen may or may not be substituted. This results in oxime or amidoxime bond formation, $R1R2C=NOR3$ where $R^1$, $R^2$, and $R^3$ can be, but are not limited to a hydrogen, alkyl, alkenyl, alkynyl group or any substitution within that group, amine, amide, oxo, or other such group. For example, an amidooxime can form from hydroxylamine and a nitrile. By "oxime", we mean to include amidooximes.

Molecules of interest are easily functionalized with protected-hydroxylamines via various substitution, displacement, and coupling reactions known in the art. Molecules of interest are also easily functionalized with aldehyde/ketones via oxidation of primary/secondary alcohols respectively, or coupling of aldehyde/ketone functionalized materials to reactive handles on the parent molecule, or other methods such as transamination reactions to modify N-termini to oxo-amides. Examples may include, but are not limited to, proteins, peptides, carbohydrates, DNA, cDNA, RNA, siRNA, neurotransmitters, drugs (synthetic or natural), or fluorophores. In addition, larger cargoes such as nanoparticles can be modified with ketones, or any of the other functionalities, and immobilized to the hydrogel.

Other synthetic polymers, such as those that are charged (i.e. negative charged such as those with sulfates or positive charged such as those with protonated amines) or contain within the structure degradable bonds such as esters, amides, carbonates, acetals, and any other degradable group or other neutral polymer may be used as one of the condensation partners for the gel. A specific example may include polystyrene sulfonate and poly(styrene sulfonate-co-polyethylene glycol methacrylate) and poly(styrene sulfonate-co-polyethylene glycol acrylate). We have shown that this polymer is a heparin mimic and binds to heparin binding protiens such as bFGF and VEGF.

Once these molecules are functionalized it is possible to conjugate/load these materials with biological cues/therapeutics or use these materials directly. Bioactive signals modified with aldehyde or ketones or oxo groups or hydroxyl amines are incorporated into the hydrogel matrix by simply mixing the polymer containing the correspondant functionality to form an oxime bond with the bioactive signal to form a covalent form (for example, a ketone modified peptide with an aminooxy modified polymer). The polymer modified with the bioactive signal can then be crosslinked using a crosslinking molecule bearing two or more aldehydes or ketones or oxo groups or hydroxyl amines. Alternatively, the bioactive cue/therapeutic can be incorporated into the gel and held there by non-covalent interactions including electrostatics. Examples of bioactive signals include ligand binding peptides and signaling proteins such as growth factors.

Subsequent combination of these materials (aldehyde/ketone with hydroxylamine) results in hydrogels. These hydrogels are capable of forming in complex solutions such as media, serum, and In the presence of cells due to the chemospecificity of the oxime bond.

Furthermore, the reaction conditions are mild and biocompatible due to the ability of oxime bond formation to occur in complex aqueous solutions over a pH range of 4-8.5. Importantly, the reaction occurs quickly ranging from a few seconds to a few hours so that point-of-care applications (i.e. delivery through a syringe) will be possible. Thus, this invention is useful as a product that can be applied at the site of tissue to repair that tissue or deliver therapeutics at a particular site or prepared beforehand and placed as a preformed gel at a site.

In one embodiment, the hydrogels gel quickly in the presence of cells and therapeutics. Suitable commercial applications include diverse applications such as wound dressings and skin grafts, tissue engineering and regenerative medicine applications (including bone or cardiac repair), drug delivery, pesticide or other plant delivery systems, cosmetics, personal care products and contact lenses.

For drug delivery, tissue engineering, and cell encapsulation, it is preferable that the chemical crosslinking reaction of the present invention be performed in aqueous media. Furthermore, in a preferable embodiment, the reaction does not utilize any metal due to toxic side effects.

In a preferred embodiment, the crosslinking method is biocompatible, in that the crosslinking functional groups before and after the reaction are not toxic. Additionaly, any byproducts, if any, are preferably non-toxic. The formed crosslink is stable for hours to months to indefinite time period depending on the functional groups surrounding the oxime bond, which is controlled by the initial chemistry under biological conditions in biological fluids and tissues and degradation products if any need to be minimized and nontoxic. The method has flexibility and one can tune the stability of the bond depending on the oxime that is formed, glyoxylamide being less stable than an oxime formed from a ketone or one that is reduced after formation, which is an advantage of the system.

In a preferred version, the crosslinking method is bioorthogonal, meaning that the crosslinking functional groups do not react significantly with other functional groups present in the cargo that is being loaded/delivered or with biological tissues or fluids. As new approaches utilizing hydrogels for drug delivery, tissue engineering, and cell encapsulation are developed, there is a need for simple and efficient crosslinking methodology that is biocompatible and bioorthogonal. Oxime bond formation is chemospecific and does not react with functional groups found in biological molecules, the byproduct is water, and the formed bond is stable. The latter is important because the gels can be made degradable by incorporation of specific degradable chemistry or by incorporation of a peptide sequence that would degrade in the presence of a specific enzyme or molecule. The reactive partners are stable and, thus, can be stored without significant change in chemical structure.

Methods of the Present Invention

In one embodiment, the present invention relates to a method of creating a hydrogel, comprising the step of condensing first and second functional groups, wherein the first group comprises a molecule or macromolecule of interest containing two or more hydroxylamine or aminooxy groups and the second group comprises a molecule or macromolecule of interest containing two or more aldehyde/ketone/other reactive oxo groups, under conditions such that a hydrogel forms. In some embodiments, the molecule of interest is identical in the first and second functional group. In other embodiments, the molecule of interest is not identical.

In one specific embodiment, the molecules or macromolecule of interest may be homopolymers or co-polymers having the general structures of

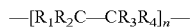

wherein $R_1$-$R_4$ are independently selected from hydrogen or a side chain comprising at least one carbon atom selected from the group consisting of -Alkyl, -Alkenyl, -Alkynyl, -Aryl, -Heteroaryl, and -Heterocyclyl.

In another specific embodiment, the molecules or macromolecules of interest may be selected from the group consisting of polyethylene glycol, polyethylene glycol (PEG) derivative, polystyrene sulfonate, poly(styrene sulfonate-co-polyethylene glycol methacrylate), polypropylene oxide, polyethylene oxide, and poly(styrene sulfonate-co-polyethylene glycol acrylate).

The present method for forming a hydrogel may be conducted under any suitable environments or conditions. In one preferred embodiment, the hydrogel in the present invention may form under mild and bio-compatible conditions, e.g., at room temperature, in aqueous solutions, and under pH=4-7.4.

In one embodiment, the molecule or macromolecule of interest in the first group may be a polyethylene glycol (PEG) derivative. Any PEG derivatives may be suitable for molecules or macromolecules of interest in the first group.

In one preferred embodiment, a suitable PEG derivative in the first group may comprises two or more groups of $NH_2$—$O$—$(CH_2CH_2O)_n$—, wherein n=1-1000.

In another embodiment, the molecule or macromolecule of interest in the second group may comprise two or more groups of $R_1CO$-L-$COR_2$, wherein $R_1$ and $R_2$ are independently selected from the group consisting of H, Cl, Br, I, -Alkyl, -Alkenyl, -Alkynyl, -Aryl, -Heteroaryl, -Heterocyclyl, $OR_3$, $SR_4$, $NR_5$, and biomolecules and L is a linker molecule. $R_3$, $R_4$ and $R_5$ are independently selected from the group consisting of H, Cl, Br, I, -Alkyl, -Alkenyl, -Alkynyl, -Aryl, -Heteroaryl and -Heterocyclyl.

As used herein, the term "linker molecule" refers to any suitable groups which are capable of linking two carbonyl groups.

In one specific embodiment, L may be selected from the group consisting of -Alkyl-, -Alkenyl-, Alkynyl-, -Aryl-, -Heteroaryl-, -Heterocyclyl-, and —$(CH_2CH_2O)n$—, wherein n=0-1000.

In one preferred embodiment, at least one biomolecule may be incorporated in the molecule or macromolecule of interest. For example, a biomolecule may be linked to the molecule or macromolecule of interest in the second group. Preferably, the biomolecules are selected from the group consisting of proteins, enzymes, antibodies, antibody fragments, peptides, and nucleic acids. A suitable nucleic acid may be selected from the group consisting of DNA, RNA, siRNA, antisense RNA, RNAi, snRNA, miRNA, and cDNA. A suitable nucleic acid may also comprise nucleic acid analogs.

In one specific embodiment, the present invention may also enclose methods and compositions for controlling release of biomolecules from a hydrogel. For this purpose, one biomolecule may be linked to the molecule or macromolecule of interest through additional chemical bonds which may be cleaved under certain conditions. In one preferred embodiment, the additional chemical bonds may be peptide bonds, and the peptide bonds may be specifically cleaved by using an enzyme such as a protease. In another embodiment, the cleavage is chemical.

In one embodiment, the molecule or macromolecule of interest in the first and second group may be a PEG derivative.

In one preferred embodiment, a suitable PEG derivative may comprise two or more groups of $R_6CO$—$(CH_2)_m$—$COO$—$(CH_2CH_2O)_n$—, where $R_6$ is selected from the group consisting of H, Cl, Br, I, -Alkyl, -Alkenyl, -Alkynyl, -Aryl, -Heteroaryl, -Heterocyclyl, —$OR_3$, —$SR_4$, —$NR_5$, and biomolecules. $R_3$, $R_4$ and $R_5$ may be independently selected from the group consisting of H, Cl, Br, I, -Alkyl, -Alkenyl, -Alkynyl, -Aryl, -Heteroaryl and -Heterocyclyl. Preferably, m=1-1000 and n=0-1000. More preferably, m=1-20 and n=0-1000.

Any biomolecules as previously discussed may be suitable for the above functional groups. One biomolecule may also be linked to the molecule or macromolecule of interest through additional chemical bonds, such as peptide bonds, for the purpose of controlling release.

In some embodiments, the first and second functional groups may include more than one type of functional groups as discussed above. For example, a hydrogel may be produced by condensing any of PEG derivatives, such as those shown above, as the first group and any of PEG derivatives, such as those shown above, as the second groups.

In one embodiment, a molecule or macromolecule of interest may include both two or more hydroxylamine or aminooxy groups and two or more aldehyde/ketone/other reactive oxo groups. Specifically, the present method for forming a hydrogel may comprise the step of condensing functional groups, wherein the functional groups comprise a molecule or macromolecule of interest containing two or more hydroxylamine or aminooxy groups and two or more aldehyde/ketone/other reactive oxo groups, under conditions such that a hydrogel forms.

In another aspect, the present invention relates to a hydrogel formed from any of the above methods.

In one specific embodiment, a hydrogel in the present invention may be bio-degradable or degradable.

In another specific embodiment, a hydrogel in the present invention may be bio-compatible.

In one embodiment, a hydrogel in the present invention may comprise a condensation product wherein the condensation product forms from condensing first and second functional groups, and wherein the first group comprises a molecule or macromolecule of interest containing two or more hydroxylamine or aminooxy groups and the second group comprises a molecule or macromolecule of interest containing two or more aldehyde/ketone/other reactive oxo groups. The first and second groups may include any functional as discussed above or any other suitable functional groups according to a person of artisan.

In another embodiment, a hydrogel in the present invention may comprise a condensation product wherein the condensation product forms from condensing functional groups, wherein the functional groups comprise a molecule or macromolecule of interest containing two or more hydroxylamine or aminooxy groups and two or more aldehyde/ketone/other reactive oxo groups, under conditions such that a hydrogel forms.

Applicants have developed a new method for synthesizing hydrogels. In its simplest form, this discovery utilizes the condensation reaction between hydroxylamine and ketone/aldehyde functionalized molecules/macromolecules to form oxime bonds. The condensation of a ketone/aldehyde with a hydroxyl amine molecule results in the generation of an oxime bond and a water molecule. This reaction exhibits high yields and chemospecificity as well as a high tolerance to a wide variety of other functional groups and reaction conditions. This method allows oxime bond formation to occur in a wide range of organic solvents and in aqueous media over a wide pH range 4-8.5. Applicants note there must be multi-functionality to form the bond. In other words, there must be two or more groups for the one reactive partner (what Applicants call the cross-linker in Grover, Lam, et al. 2012) and four or more groups for the other partner. It doesn't matter which functionality is on which partner. The Example and Grover, Lam, et al. (Grover, Lam, et al. 2012) disclose the dialdehyde on the cross-linker and the aminooxy on the PEG polymer, but it could easily be the opposite.

In one aspect of this invention, molecules of interest and/or macromolecules (hydrogel precursors) may be functionalized with hydroxyl amine and/or ketones or aldehydes to create a functional group. The phrase "functional groups" refers to molecules or macromolecules containing one or more hydroxyl amines and/or aldehydes/ketones/other oxo group. An "oxo group" refers to the group of C=O. "Oxo" may include aldehydes, ketones, oxoamides, acyl halide (e.g., chloro, bromo, and iodo), carboxylate, and other suitable groups.

"Molecules of interest" refers to any organic compounds with formula weights less than 1000 g/mol. "Macromolecules" refers to any organic compounds with molecular weights greater than or equal to 1000 g/mol. This may include peptides, proteins, synthetic polymers, and biologically derived materials. "Peptide" refers to oligomers of ten or less amino acids linked by amide bonds. "Protein" refers to polymers of amino acids linked by amide bonds that can or cannot contain additional functionality such as cofactors, lipids, and polysaccharides. "Synthetic polymers" refers to chains of organic molecules that are fabricated by polymerization techniques such that they include hydroxyl amines or ketone/aldehyde, or precursors/reactive handles to install hydroxyl amines or ketone/aldehydes post polymerization. "Biologically derived materials" refers to linear and branched polysaccharides that contain or can be functionalized with hydroxyl amines, aldehydes, and/or ketones and/or any other oxo compounds such as an oxo amide.

To form a hydrogel through oxime bond formation, a polymer bearing more than two hydroxyl amines is mixed with a molecule or polymer bearing more than two aldehydes/ketones. Upon mixing of these functionalized molecules/macromolecules, oxime bond formation occurs resulting in liquid to solid/gel transition (see FIG. 1). As an illustrative example, Applicants demonstrated this invention using a small molecule dialdehyde that upon mixing with an branched polymer functionalized with eight aminooxy groups formed an oxime linked hydrogel. (Note that aminooxy and hydroxyl amine are interchangeable terms.)

This discovery also demonstrates that these gels are biocompatible. Therefore, these gels may be able to load biological cues/deliver therapeutics and to encapsulate cells.

As used herein, the term "biological cues" refers to any agents or substances that interact with cells in a way that can change or maintain the cell behaviour. For example, a biological cue may be a feature such as surface pattern or functionality (peptide, protein, functional group etc.), that cells can use as a guide to elicit a directed response.

As used herein, the term "therapeutics" or "therapeutic agents" refers to any compound useful for therapeutic or diagnostic purposes. The terms as used herein are understood to mean any compound that is administered to a patient for the treatment of a condition that can traverse a cell membrane more efficiently when attached to a nanoparticle of the disclosure than when administered in the absence of a nanoparticle of the disclosure.

Therapeutic agents include but are not limited to hydrophilic and hydrophobic compounds. Accordingly, therapeutic agents contemplated by the present disclosure include without limitation drug-like molecules, proteins, peptides, antibodies, antibody fragments, aptamers and small molecules.

Protein therapeutic agents include, without limitation peptides, enzymes, structural proteins, receptors and other cellular or circulating proteins as well as fragments and derivatives thereof, the aberrant expression of which gives rise to one or more disorders. Therapeutic agents also include, as one specific embodiment, chemotherapeutic agents. Therapeutic agents also include, in various embodiments, a radioactive material.

In the present invention, the term "hydrogels" and "gels" may be used interchangably.

In one embodiment of the invention, molecules/macromolecules may be functionalized with hydroxylamines and aldehydes/ketones/oxo groups. In another embodiment, therapeutics or biological cues may be conjugated to the ketone/aldehyde molecules/macromolecules or conjugated to the hydroxylamine molecules/macromolecules to generate loaded materials still capable of crosslinking. The one embodiment of this invention, the cross-linking of the loaded materials occurs in the presence of serum or media at various pHs in the presence of cells. The cells exhibit high viability and are influenced by the loaded materials. Furthermore, the choice of materials utilized allows for tuning the biodegradation (if any) of the material.

Figure 9:
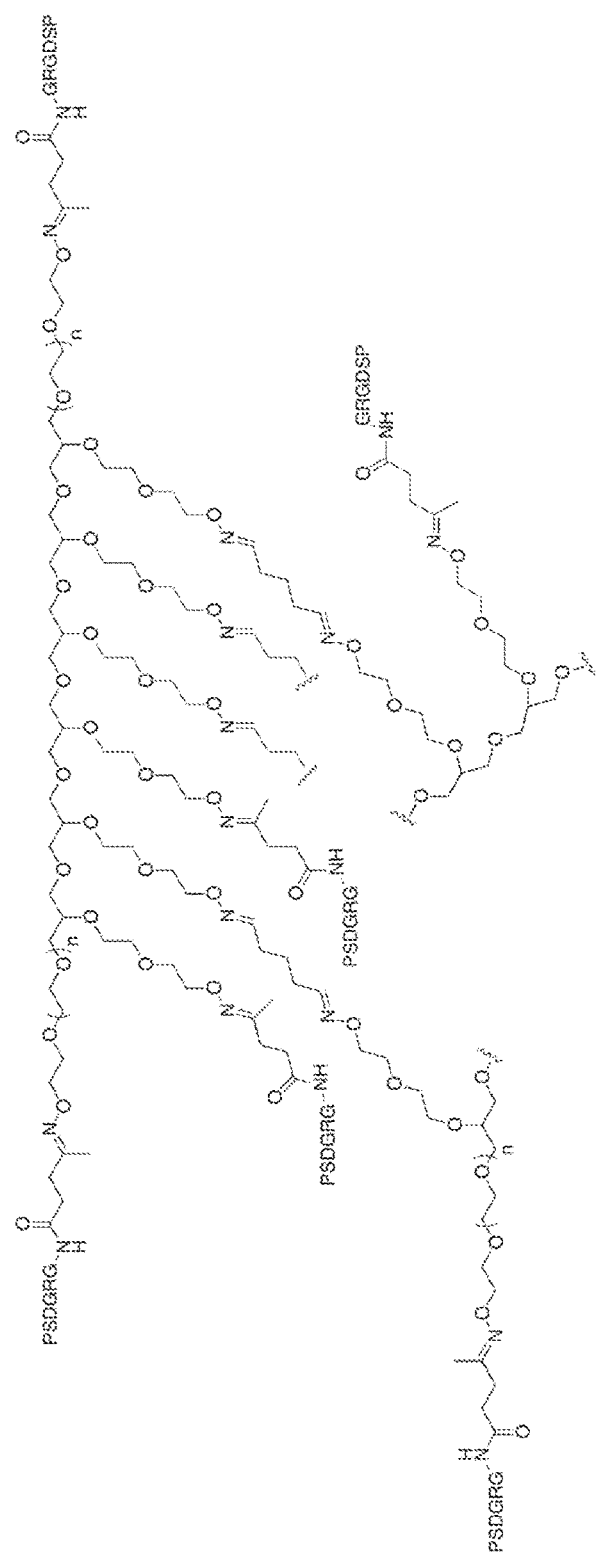
FIG. 9 is a pictures showing an exemplary gel structure according to one embodiment of the present invention.
Figure 10:
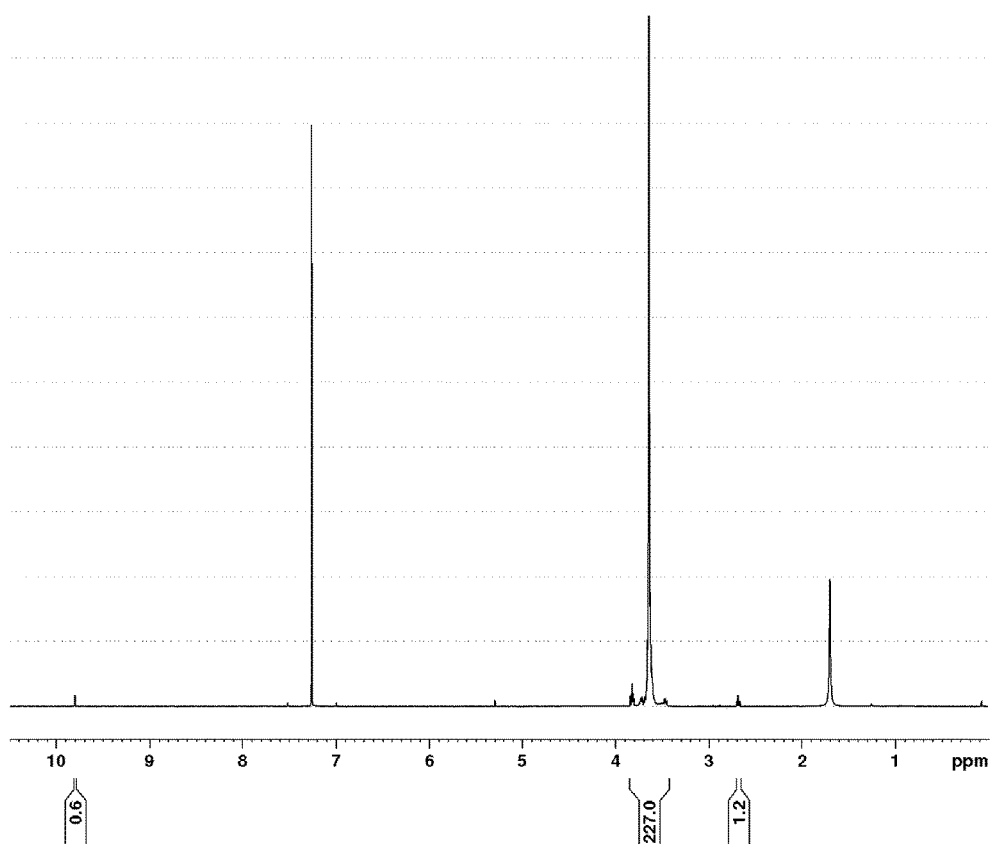
FIG. 10 is a picture showing NMR spectra of PEG-aldehyde.

In one embodiment, the present invention relates to a hydrogel produced using any the above methods. In one specific embodiment, the hydrogel mya be those comprising branched polyethylene glycol (PEG) crosslinked via oxime bonds. Example and Grover, Lam, et al. (Grover, Lam, et al. 2012) disclose a hydrogel comprising branched polyethylene glycol (PEG) crosslinked via oxime bonds through the use of glutaraldehyde. The hydrogel consists of PEG units linked to other PEG units via a short alkyl chain. The link itself is an oxime bond formed from an aldehyde and O-hydroxylamine. FIG. 9 shows a drawing of an exemplary gel of the present invention. FIG. 9 also discloses a hydrogel after formation that includes RGD peptide.

As an illustrative example, we have utilized branched PEG aminooxy and glutaraldehyde as the reactive partners. However, as stated above, any hydroxyl amine and oxo group source can be utilized. Example and Grover, Lam, et al. (Grover, Lam, et al. 2012) show specific chemical drawings and experimental details for these embodiments.

In one embodiment of the present invention, functionalized polymers will be sold as part of a kit, preferable containing a hydroxyl amine functionality and a ketone/aldehyde functionality. Upon mixing the two components, in the desired buffer and PH and together with the desired additives such as biological cues, drugs or cells, the hydrogel forms. The additives such as biological cues, drugs or cells may be suitable for the present invention. Any other additives may also be suitable for the present invention. Suitable biological signals may include peptides that contain ligands for cell adhesion such as Arg-Giy-Asp, bFGF, VEGF, PDGF and KGF.

In some embodiments, one might substitute haluronic acid or heparin as the biological polymer instead of PEG. Other biologically derived or synthetic polymers would be suitable.

In one aspect, the present invention relates to a kit for using the hydrogel formed from any of the above methods. The kit may be used for experimental purposes in the lab or for biomedical purposes. For the latter application, a delivery device such as a two part syringe may be useful.

The hydrogel can then be used as a drug delivery device, a scaffold for tissue engineering, or a scaffold for stem cell transplantation.

In another aspect, the present invention relates to storing and delivering cells. Any type of cells may be suitable for the present invention. In one specific embodiment, the hydrogel in the present invention may be used to store and deliver stem cells.

In one embodiment, cells or cell seeds may be initially mixed with first or second functional groups, wherein the first group comprises a molecule or macromolecule of interest containing two or more hydroxylamine or aminooxy groups and the second group comprises a molecule or macromolecule of interest containing two or more aldehyde/ketone/other reactive oxo groups. When the first and the second functional groups undertake a condensation reaction to form a hydrogel, the cells are stored and deliverable in the hydrogels. In another related embodiment, the cells may be seeded on top of the hydrogel.

Specifically, the molecules or macromolecules of interest in the hydrogel may be homopolymers or co-polymers having the general structures of

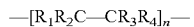

—[$R_1R_2C$—$CR_3R_4$]$_n$— wherein $R_1$-$R_4$ are independently selected from selected from hydrogen or a side chain comprising at least one carbon atom selected from the group consisting of -Alkyl, -Alkenyl, -Alkynyl, -Aryl, Heteroaryl, Heterocyclyl, Halogen, and Hydrogen.

In one embodiment, the molecules or macromolecules of interest are selected from the group consisting of polyethylene glycol, polyethylene glycol (PEG) derivative, polystyrene sulfonate, poly(styrene sulfonate-co-polyethylene glycol methacrylate), poly(styrene sulfonate-co-polyethylene glycol acrylate), polypropylene oxide, and polyethylene oxide.

In another specific embodiment, the molecule or macromolecule of interest in the first group is a polyethylene glycol (PEG) derivative. A suitable PEG derivative may comprise two or more groups of $NH_2$—O—$(CH_2CH_2O)_n$—, wherein n=1-1000.

In another specific embodiment, the molecule or macromolecule of interest in the second group is a polyethylene glycol (PEG) derivative. A suitable PEG derivative may comprise two or more groups of $R_6CO$—$(CH_2)_m$—COO—$(CH_2CH_2O)_n$—, where $R_6$ is selected from the group consisting of H, Cl, Br, I, -Alkyl, -Alkenyl, -Alkynyl, -Aryl, Heteroaryl, Heterocyclyl, OR3, SR4, NR5, and biomolecules wherein m=1-1000 (preferably m=1-20) and n=0-1000. R3, R4, R5 are independently selected from the group consisting of H, Cl, Br, I, -Alkyl, -Alkenyl, -Alkynyl, -Aryl, Heteroaryl, and Heterocyclyl. Biomolecule may be selected from the group consisting of proteins, peptides, enzymes, antibodies, nucleic acids and cellular components, and the nucleic acid may be selected from the group consisting of DNA, RNA, siRNA, and cDNA.

In another specific embodiment, wherein the polyethylene glycol (PEG) derivative in the second group may comprise two or more groups of HCO—$(CHR)_m$—O—$(CH_2CH_2O)_n$—, wherein m=1-1000 (preferably m=1-20) and wherein n=0-1000 and wherein R may be selected from the group consisting of H, -alkyl, —$CCl_3$, aryl, and $CH_2Cl$.

In one embodiment, a method for storing and delivering cells may comprise the steps of mixing cells with either first or second functional groups, wherein the first group comprises a molecule or macromolecule of interest containing two or more hydroxylamine or aminooxy groups and the second group comprises a molecule or macromolecule of interest containing two or more aldehyde/ketone/other reactive oxo groups. Specifically, the molecule or macromolecule of interest in the first and the second functional groups may simutaneously be PEG derivaties as discussed above.

Figure 4:
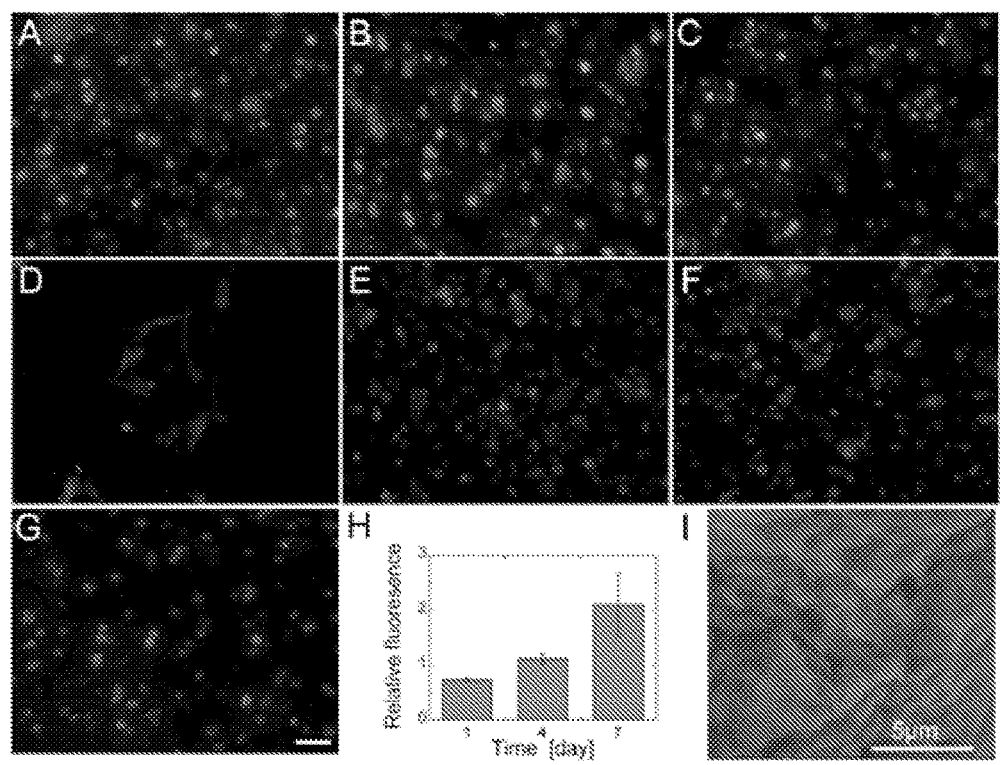
FIG. 4 is a set of images and graphs showing an example of the bio-application of as prepared hydrogels. Live/Dead staining of the encapsulated mouse MSCs shows good viability at (FIG. 4A) day 1, (FIG. 4B) day 4, (FIG. 4C) and day 7.

In another embodiment, a hydrogen may be formed first following any of the above methods, and cells or cell seeds may be placed on the top of the hydrogel. FIG. 4 and the Example show one of such embodiments.

Applicants envision that in certain embodiments, the molecule or macromolecule of interest in the hydrogel may be modified to allow the cells or cell seeds to be placed inside of the hydrogel after the formation of the hydrogel.

In one embodiment, any methods for making porous hydrogels may be suitable for the modification of hydrogels. Modifications may be performed during the fabrication of hydrogels. One approach may include forming the hydrogel in an organic solvent with porogens such as salt or sugar particles and subsequently leaching out the porogens in water. Another approach may include using a non-reactive low MW PEG as a porogen to form a porous structure after leaching out the PEG. Alternatively, a crystallizable solvent such as ethylene carbonate may be used and then leached out with cold water. Additive manufacturing techniques may also be used to make porous hydrogels.

In another aspect, the present invention relates to a method for controlling release of a biomolecule from a polymer or copolymer composition. In one embodiment, the present method for controlling release may be applicable to release any suitable biomolecule from any suitable polymer or copolymer composition. The term "biomolecule" as used herein refers, but is not limited to proteins, peptides, enzymes, antibodies, nucleic acids (such as DNA, cDNA, RNA, siRNA, and others) cellular components and pharmaceutical compositions.

In one preferred embodiment, the biomolecule to be released may be a peptide, a polypeptide, or a protein. The term "polypeptide", as used herein, refers to any single linear polymer chain of amino acids bonded together by peptide bonds between the carboxyl and amino groups of adjacent amino acid residues. In another preferred embodiment, a suitable polymer or copolymer composition may include any compositions for forming a hydrogel, e.g., those as discussed above. More preferably, suitable compositions for forming a hydrogel may include any monomers which form a hydrogel under beign conditions, e.g., at room temperature, in aqueous solutions, and the solutions having suitable pH values. Suitable pH values may be in the range of 4-8, preferably in the range of 4-7.4.

A suitable reaction for forming a hydrogel to control release a biomolecule may be a condensation reaction. The term "condensation" or "condensation reaction", as used herein, refers to a chemical reaction in which two molecules or moieties (functional groups) combine to form a larger molecule, together with the loss of a small molecule. Possible small molecules lost may include water, hydrogen chloride, methanol, or acetic acid. A condensation or condensation reaction may also commonly refer to dehydration synthesis. When two separate molecules react, the condensation may be termed intermolecular. A simple example is the condensation of two amino acids to form the peptide bond characteristic of proteins.

In one embodiment, the biomolecule to be released may not be chemically linked to the molecule or macromolecule of interest in the hydrogel. There may be no chemical bonds between the biomolecule to be released and the hydrogel. For example, the biomolecule may be attached to the hydrogel by electrostatic force, hydrogen bond, or any other suitable interaction in the absence of chemical bond formation. In this embodiment, the biomolecule may be controllably released by removing or decreasing the force or the interaction between the biomolecule and the hydrogel. For example, the force or the interaction between the biomolecule and the hydrogel may be removed or decreased by cleaving chemical bonds which are critically involved in the interaction.

In one preferred embodiment, the biomolecule to be released may be linked to the molecule or macromolecule of interest in the hydrogel through chemical bonds. Any chemical bonds may be used to link the biomolecule with hydrogels. In one specific embodiment, the chemical bond may be bio-degradble bonds such as peptide bonds. Certain enzymes may degrade specific peptides. For example, a matrix metalloproteinase (MMP) may specifically degrade the peptide sequence between the residues of GPQG and IWGQ. There are other MMP cleavable peptide sequences such as L|GPA (by MMP-1), GPQG|IAGQ (by MMP-1), PEN|FF (by MMP-13).

In one specific embodiment, peptide sequences may be modified to include some residues reactive with functional groups of the polymers to make the hydrogels. For example, the sequence used to make the hydrogels may have two levulinic acid residues (Lev-GGPQG|IWGQG-Lev-GL) to react with aminooxy groups of the polymer.

A peptide having a similar sequence may be chemically synthesized. For example, a peptide having a sequence of Gly-Gly-Gly-Pro-Gln-Gly-Ile-Trp-Gly-Gln-Gly which was synthesized may still be degradable by MMP. Therefore, a system for controlling release a biomolecule may be designed by chemically link the biomolecule with molecule or macromolecule of interest in the hydrogel through a peptide of Gly-Gly-Gly-Pro-Gln-Gly-Ile-Trp-Gly-Gln-Gly. In the presence of MMP, the peptide of Gly-Gly-Gly-Pro-Gln-Gly-Ile-Trp-Gly-Gln-Gly would be degraded, and the biomolecule would be subsequently release from the hydrogel.

Applicants envision that such a controlled release mechanism would be applicable to any suitable enzymes which degrade specific peptide sequences. For example, Zelzer, Simon, et al. disclosed the list of enzymes which degrade certain specific peptide sequences (Zelzer, Simon, et al., 2013).

In one preferred embodiment, the biomolecule is a polypeptide. In one specific embodiment, the present method for controlling release of a polypeptide from a hydrogel into an environment, the method comprising the step of: a) forming a hydrogel according to any of the methods discussed above, wherein the molecule or macromolecule of interest in the hydrogel further comprises a polypeptide and wherein a chemical bond forms between the polypeptide and the molecule or macromolecule of interest in the hydrogel; b) placing the hydrogel in an environment, and adding an enzyme such as a protease into the environment; and c) allowing the enzyme to cleave the chemical bond between the polypeptide and the molecule or macromolecule of interest in the hydrogel and releasing the polypeptide into the environment.

In one specific embodiment, the chemical bond may be a peptide bond as discussed above, and the enzyme may be a protease such as MMP which is capbale of degrading a peptide bond in a specific peptide sequence.

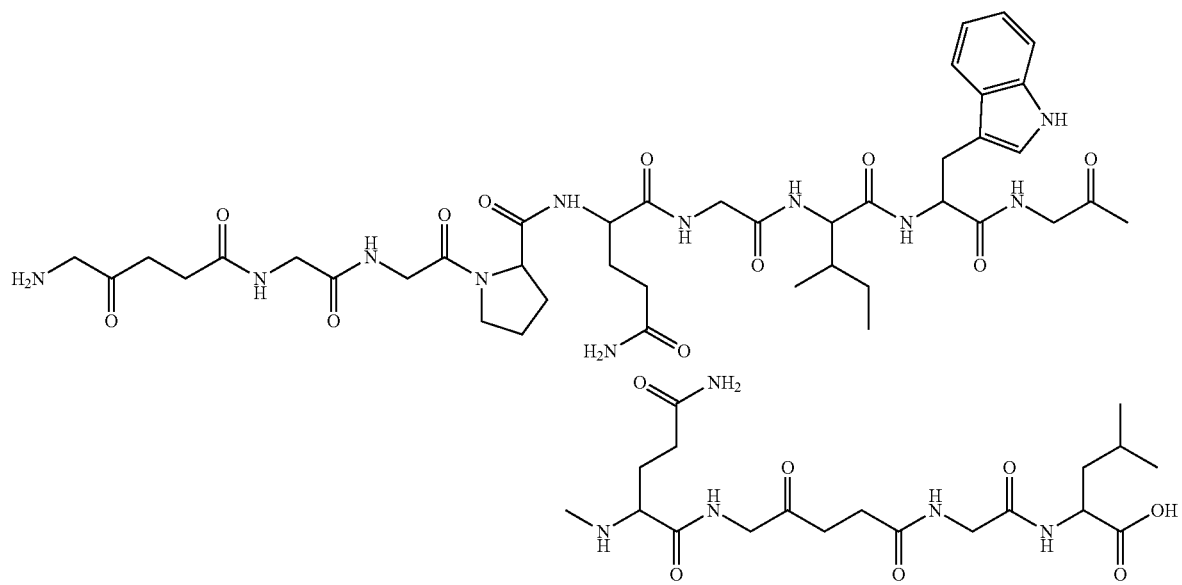

EXAMPLES

Example 1

Experimental

Materials and Methods

The 8-armed aminooxy polyethylene glycol (AO-PEG) was synthesized as previously described (Scheme 1) (Christman, Schopf, et al., 2009). All other reagents were purchased from Sigma Aldrich (St. Louis, Mo.) or Fisher Biotech (Pittsburgh, Pa.) and utilized as received unless otherwise indicated. Mass spectra were acquired using an Applied Biosystems Voyager-DE-STR MALDI-TOF instrument or a Thermo Finnigan LCQ Deca Ion Trap MS instrument. $^1$H, $^{13}$C NMR and COSY spectroscopy were performed on an Avance DRX 400 or 500 MHz spectroscopy instruments. Infrared spectroscopy was recorded on a PerkinElmer FT-IR equipped with an ATR accessory.

droxyphthalimide tetra(ethylene glycol) (100 mg, 0.29 mmol) dissolved in 1 ml of dry acetonitrile in a 15-ml scintillation vial. The reaction was allowed to stir for 12 hours at 23° C. The reaction was filtered through a 0.2 μm PTFE filter to remove the white precipitate. The supernatant was collected and allowed to stand in a sealed scintillation vial for 30 min. The solution was then filtered again to remove the newly formed precipitate. The collected supernatant was subjected to lyophilization until complete dryness to yield the desired product (39 mg, 65% yield). $^1$H NMR (400 MHz, CDCl$_3$) δ 3.89-3.88 (m, 2H, CH$_2$ONH$_2$), 3.76-3.72 (m, 12H, ethylene glycol protons), 3.67-3.65 (m, 2H, CH$_2$OH) ppm; $^{13}$C NMR (400 MHz, CDCl$_3$) δ 74.2, 71.7, 69.6, 69.6, 69.5, 69.4, 68.5, 60.3 ppm; IR (neat): 3348, 3072, 3050, 2957, 2931, 2892, 2857, 1702, 1589, 1505, 1427, 1361, 1267, 1237, 1211, 1111, 915 cm$^{-1}$.

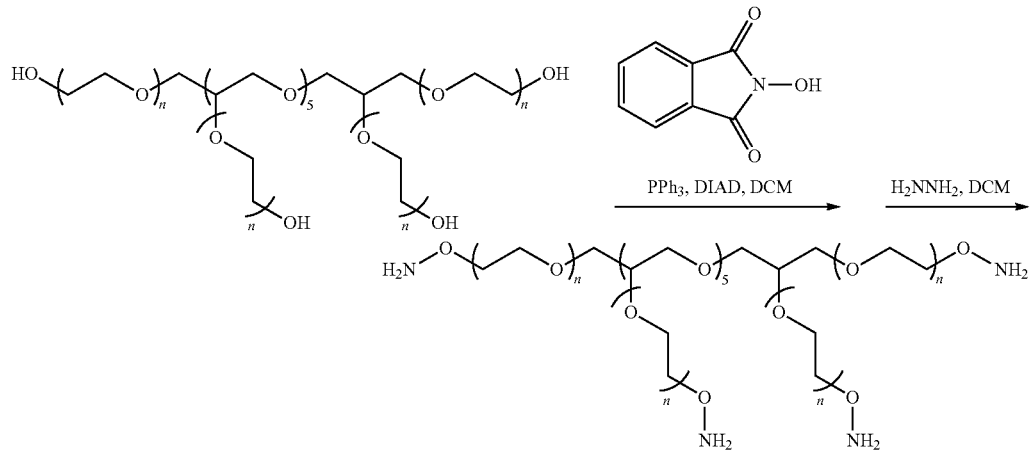

Scheme 1. Synthesis of eight arm aminooxy PEG.

Synthesis of O-Hydroxylamine Tetra(Ethylene Glycol)

Tetra(ethylene glycol) (16.60 g, 0.085 mol) was dissolved in 10 ml of dichloromethane in a two-neck round bottom flask. To that, N-hydroxyphthalimide (1.75 g, 0.011 mol) and triphenylphosphine (Ph$_3$P) (2.80 g, 0.011 mol) were added sequentially under argon. Then, diisopropyl azodicarboxylate (DIAD) (2.11 ml, 0.011 mol) was added drop wise to the solution mixture using an additional funnel. The reaction was stirred under argon for 16 hours at 23° C. The intermediate N-hydroxyphthalimide tetra(ethylene glycol) was purified via flash silica gel chromatography. First, the column chromatography was run with 1:2 v/v hexane:ethyl acetate until the triphenylphosphine oxide eluted. Then, the mobile phase was switched to 100% ethyl acetate to elute the desired compound (R$_f$=0.27, 2.10 g, 58% yield). $^1$H NMR (400 MHz, CDCl$_3$) δ 7.84-7.81 (m, 2H, aromatic Hs, CCHCH), 7.76-7.72 (m, 2H, aromatic Hs, CCHCH), 4.39-4.36 (m, 2H, CH$_2$ON), 3.87-3.57 (m, 14H, ethylene glycol protons) ppm; $^{13}$C NMR (400 MHz, CDCl$_3$) δ 163.4, 134.5, 128.9, 123.5, 77.2, 72.5, 70.7, 70.5, 70.4, 70.3, 69.2, 61.7 ppm; IR (neat): 3473, 2869, 1788, 1725, 1611, 1466, 1374, 1291, 1248, 1186, 1120, 1081, 1065, 1028, 977, 952 cm$^{-1}$; MS (ESI-MS) calc. for C$_{16}$H$_{21}$NO$_7$Na$^+$: 362.12 observed: 362.17.

Cleavage of the N-phthalimide was accomplished by adding anhydrous hydrazine (200 μl, 6.2 mmol) to N-hy-

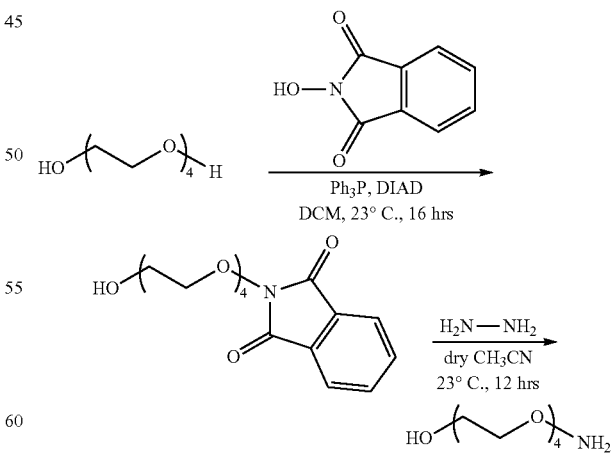

Scheme 2. Synthesis of O-hydroxylamine tetra(ethylene glycol)

NMR Study of Model System

O-Hydroxylamine tetra(ethylene glycol) (22 mg, 0.10 mmol) was dissolved in 0.8 ml of D$_2$O and loaded into an NMR tube. To this, glutaraldehyde (25% aqueous solution, 24 μl, 0.05 mmol) was added to the NMR tube. The NMR tube was inverted a few times to mix, then let stand at 23° C. for 1.5 hours prior to NMR spectroscopy. The pH of the solution after the studies was 4.

Scheme 3. Model study for hydrogel formation (note: major project shown).

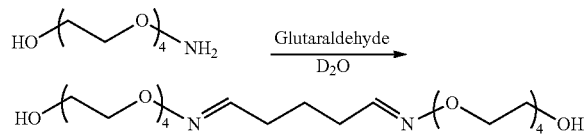

Synthesis of RGD-containing Peptide

The lev-GRGDSPG adhesion peptide was synthesized using standard solid-phase peptide synthesis methods with a 2-chlorotrityl chloride resin and HBTU (O-(Benzotriazol-1-yl)-N,N,N',N'-tetramethyluronium hexafluorophosphate). A ketone was added to the N-terminus of the peptide, $NH_2$-GRGDSPG-OH, via HBTU coupling with Fmoc-5-aminolevulinic acid (AnaSpec, Inc., Fremont, Calif.) on the resin. The side chains were deprotected and the peptide cleaved from the resin with trifluoroacetic acid (TFA)/triisopropylsilane (TIS)/water mixture (95:2.5:2.5, volume:volume:volume) at 24° C. for 4 hours. Following resin removal by filtration through a 0.4 mm PTFE syringe filter, the solution was precipitated into diethyl ether. The sample was further purified through preparative reverse-phase HPLC on a Luna 5 mm C18 column (Phenomenex, Inc., Torrance, Calif.) under a linear gradient from 95:5 to 5:95 of water/acetonitrile (containing 0.1% of trifluoroacetic acid) at 10 mL/min. Electrospray ionization mass spectrometry (MALDI, DHP, positive mode) verified the molecular weight of the $NH_2$-lev-GRGDSP-OH peptide+H: m/z 701.30 [$(M+H)^+$, calculated 701.31].

Cells

Mouse mesenchymal stem cells (mMSCs, D1, CRL12424) were purchased from ATCC (Manassas, Va., USA) and cultured in Dulbecco's modified eagle's medium (DMEM, Sigma-Aldrich) with 10% bovine growth serum (BGS, Hyclone, Logan, Utah) and 1% penicillin/streptomycin (Invitrogen, Grand Island, N.Y.). They were cultured at 37° C. with 5% $CO_2$ using standard protocols.

Gelation with mMSCs

AO-PEG was dissolved in phosphate buffered saline (PBS, pH=6, 7.2 or 8) for 20 minutes at 37° C. Lev-GRGDSPG adhesion peptide dissolved in PBS was added to the appropriate amount of dissolved PEG and allowed to react for 20 minutes at 37° C. For encapsulated cell experiments, full culture DMEM and D1 mMSC's (5,000 cells/mL final concentration) were mixed in with the PEG-RGD solution. A frozen aliquot of 0.7% glutaraldehyde in PBS was thawed and the appropriate amount added to the gel precursor solution. 10 mL gels were pipetted onto, and sandwiched between two Sigmacote functionalized glass cover slips and placed into an incubator for 30 minutes at 37° C. to gel. For 2D cell experiments, D1 cells were seeded on top of pre-formed gels.

Rheology 40 mL gels without RGD and cells were made as above and swollen overnight in 1× PBS. They were cut to size using a 8.0 mm biopsy punch and the modulus was measured with a plate-to-plate rheometer (Physica MCR 301, Anton Paar, Ashland, Va.) using a 8 mm plate with an angular frequency range of 0.1 to 10 under a constant strain of 1% at 37° C. An evaporation blocker system was used to keep the hydrogel from dehydrating during the test. To measure the time course of gelation, the gel precursor solution was pipetted onto the bottom plate of the rheometer right after the glutaraldehyde was added. The modulus was measured under a constant strain of 1% at a frequency of 1/s at 37° C. for 30 minutes. Gels were made in triplicate for each condition.

Swelling

Gels without cells and RGD were weighed immediately following their gelation ($M_g$). After swelling overnight in $H_2O$, the gels were weighed again ($M_s$). The dry weight was determined by weighing lyophilized gels ($M_l$). The swelling ratio was quantified by dividing the swollen weight by the non-swollen weight ($M_s/M_g$). The percent water in the gels was calculated by dividing the gel's water weight by the gel's total weight ($(M_s-M_l)/M_s$). Gels were made in triplicate for each condition Fixing/Imaging Gels were rinsed in 1× PBS and fixed in 4% paraformaldehyde for 30 minutes at room temperature. Following a rinse in 1× PBS, the gels were incubated in 0.1% Triton X-100 to permeate the cell membranes. Another 1× PBS rinse was followed by a 90 min incubation in rhodamine phalloidin (Invitrogen) diluted 1:40 in a 1% BSA solution at room temperature in the dark. The gels were washed 3 times with 0.05% Tween-20 for 5 min prior to imaging with an inverted fluorescence microscope (Zeiss Axio Observer). For 2-D cell seeding experiments, a single image was taken of the gel surface. For 3-D cell encapsulation experiments, 40 Z-stack slices were taken of the gel and the maximum intensity projection was taken following deconvolution image processing.

MTT Proliferation Assay

Gels containing encapsulated cells were given 100 mL of fresh media. 20 mL of MTT reagent (CellTiter 96R Aqueous One Solution Cell Proliferation Assay, Promega, Madison, Wis.) was added to each gel and incubated at 37° C. for 2 hours. 10% sodium dodecyl sulfate was added to each gel and the solutions transferred to a new plate. Absorbance was measured using a standard plate reader at 490 nm. Three gels were used at each time point.

Example 2

Hydrogels and Methods of making Hydrogels

Hydrogels are a common class of biomaterials utilized in a wide range of applications including as tissue engineering scaffolds, drug delivery vehicles, or as space filling agents. As a result, there is a tremendous amount of work in rapidly gelling materials. Although many naturally-derived materials have been exploited for these purposes, (Christman, Lee 2006) the difficulties associated with the risk of diseases, host immune response, batch-to-batch variability, and tuning properties have increasingly led to the use of wholly synthetic materials. The properties of synthetic materials can be easily tuned, including the rate of gelation, as well as mechanical strength. (Yu, Ding 2008; Fisher, Khademhosseini, et al. 2010; Eisenbarth 2007; Lutolf, Hubbell 2005) In addition, it is often possible to dial in sophisticated function such as cellular cues and ligands. (Lutolf, Hubbell 2005) There are two main methods of gelation for synthetic materials. Stimuli triggered gelation in which an external stimulus is applied to the liquid form of the material resulting in gel formation. Stimuli include temperature, pH, light or injection into aqueous environment. The other method is based upon mixing of two liquid components, and gelation in this case is a result of efficient cross-linking reactions between the two components or rapid self-assembly. (Wang, Zhou 2010) Typically, reactions in which the kinetics and the efficiency of the reaction can be tuned are desirable for these applications (i.e. the gelation time can be controlled). Herein, we describe for the first time, the use of oxime Click chemistry as a way to form hydrogels by mixing two components (FIG. 1).

Click chemistries are increasingly utilized to form hydrogels. (Nimmo, Shoichet 2011) The most commonly employed systems are the reaction of thiols with activated disulfides, maleimides, acrylates, or vinyl sulfones. (Nimmo, Shoichet 2011) These Michael addition reactions occur in aqueous buffer and have been widely used to covalently link proteins and integrin binding peptides to polymer matrices, as well as to cross-link star PEG with enzymatically degradable linkers. (Liu, Tian et al. 2010; Paterson, Hubbell 2010) Thiol-ene click has been utilized by combining multi-armed thiolated PEG, alkene- and acrylate-functionalized small molecules, and photoinitiators. (Yang, Long, et al. 2011) Norborene functionalized PEG has been cross-linked with an enzymatically degradable linker via photoinitated thiol-ene allowing for spatial and temporal control of the synthesis of an enzymatically degradable hydrogel. (Fairbanks, Schwartz et al. 2009) While thiol chemistry has been extensively used for hydrogel formation, it is sensitive to oxygen resulting in disulfides; in addition, native cysteine and amine residues can compete with the desired thiol during hydrogel formation. Huisgen cycload-dition has also been employed in the synthesis of PEG gels using a degradable peptide as the cross-linker. (Yang, Jacobsen 2010) However, for cell encapsulation this approach could be problematic due to the use of the copper catalyst for cross-linking. Copper-free azide-alkyne click reactions have been recently utilized to circumvent this difficulty. (DeForest, Anseth 2011).

Oxime Click chemistry, the reaction between an aminooxy group and an aldehyde or ketone, is ideal for hydrogel formation. The reaction is fast, orthogonal to functionalities found in biomolecules and cells, the byproduct is water, and a catalyst is not required. (Kalia, Raines 2008) Moreover, the reaction partners are stable compared to thiols. As a result, oxime chemistry has been used to modify surfaces with proteins, peptides, and DNA. (Christman, Broyer et al. 2011) The reaction has also been employed to prepare protein-polymer conjugates, (Heredia, Tolstyka et al 2007) modify cell surfaces, (Zeng, Ramya et al. 2009) and even label tissues in vivo. (Baskin, Dehnert et al. 2010) For hydrogel materials, this approach like other click chemistries, should allow for covalent incorporation of signaling molecules, particularly since proteins and peptides can be easily modified with ketones, oxoamide, or aminooxy groups. Thus, we explored the use of eight-armed aminooxy PEG (AO-PEG) and glutaraldehyde as a novel approach to hydrogels for cell incorporation (FIG. 1).

PEG was targeted as the scaffold material because it is bioinert and biocompatible, (Mimeault, Hauke et al. 2007; Yang, Ding 2008; Zhu 2010) and multi-armed PEGs have been widely used to form hydrogels. (Lutolf, Hubbell 2005; Zhu 2010) AO-PEG was synthesized by Mitsunobu reaction of N-hydroxyphthalimide with 8-arm hydroxyl terminated PEG star, followed by reduction with hydrazine (see Scheme 1). (Christman, Schopf et al. 2009) Glutaraldehyde was utilized as a readily available crosslinker for the oxime hydrogels. The molecule is reported to exist as a mixture of species ranging from oligomers/polymers to cyclic hemiacetals depending on the conditions. (Migneault, Dartiguenave et al. 2004) Because of the variety of ways this molecule can possibly react, a model system was utilized to confirm that oxime bond formation would occur. Glutaraldehyde was mixed with O-hydroxylamine tetra(ethylene glycol) in deutrated water and studied by $^1$H and $^{13}$C NMR spectroscopy.

Since the small molecule aminooxy compound could not cause cross-linking, yet had the same chemical structure as the end group of the polymer, it provided for straightforward analysis of the system. Upon mixing of the two substrates, the oxime peaks (syn and anti) where observed in the $^1$H NMR spectrum at 7.6 and 6.9 ppm, respectively (see FIG. 6a); the aldehyde peak observed in the starting glutaraldehyde solution at 9.7 ppm was no longer visible. The presence of the oxime species was confirmed by $^{13}$C NMR spectroscopy, where the peak at 154 ppm, corresponding to the oxime carbon was seen (see FIG. 6b). The results demonstrate that upon addition of glutaraldehyde to a hydroxyl amine, reaction by oxime bond formation occurs. Although we can not rule out that the other species may be present in the glutaraldehyde solution that react by different mechanisms, this model study strongly suggests that the predominant species is likely to be oxime bond formation during hydrogel formation.

Figure 2:
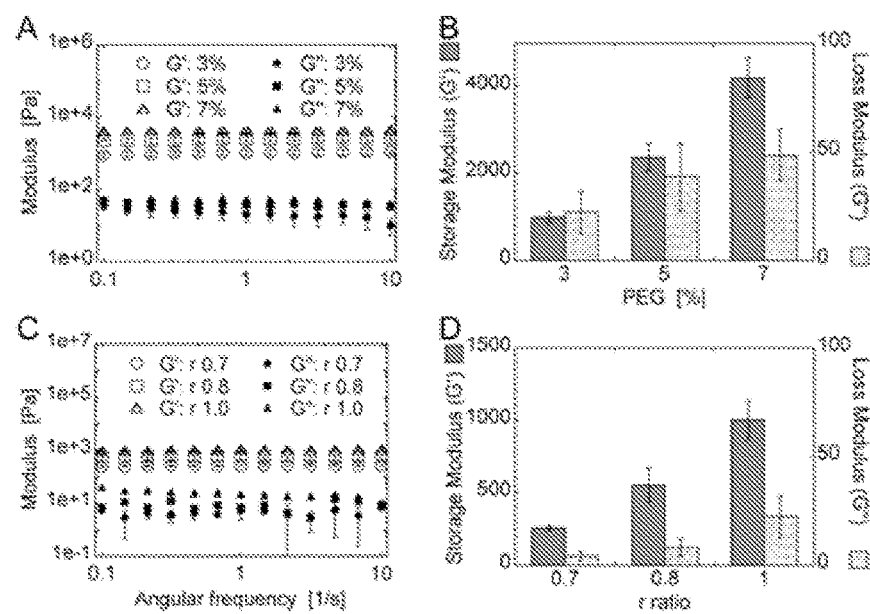
FIG. 2 is a set of graphs showing mechanical characterization of AO-PEG/glutaraldehyde hydrogels. Storage and elastic modulus can be modified by adjusting PEG polymer percentage and/or the r ratio.

Rheology was used to assess the stiffness and gelation kinetics of oxime hydrogels. A series of gels were formed with different AO-PEG weight percent with an r=1.0 (moles of aldehyde/moles of aminooxy) or different r ratios and an AO-PEG concentration of 3 weight percent (wt %) (FIG. 2). The AO-PEG/glutaraldehyde system was able to produce hydrogels with a wide range of mechanical properties, from 258 Pa (3% PEG, r ratio=0.7) to 4196 Pa (7% PEG, r ratio=1.0). The results of the rheology demonstrate that this system is able to generate materials with a broad range of mechanical properties similar to soft tissue. This is important because mechanical properties have been shown to play a key role in determining cell fate.

Figure 3:
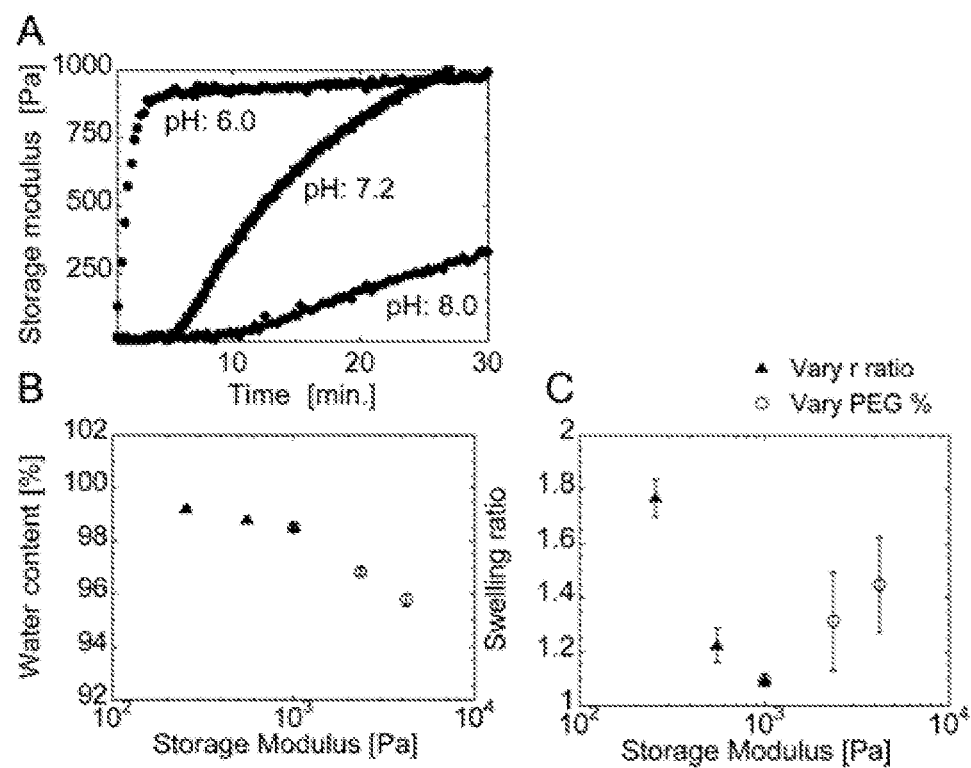
FIG. 3 is a set of graphs showing that hydrogel gelation kinetics can be altered by adjusting the pH of the solution.

The ability to tune the rate of gelation is critical for Click chemistry-induced gelation, where crosslinking is initiated immediately following crosslinker addition. Rapid gelation does not readily allow for the homogeneous incorporation of cells, yet if gelation is too slow, it might not be able to be used as an injectable hydrogel in vivo. Since oxime bond formation is acid catalyzed we investigated the rate of gelation over a range of pH values. Gelation kinetics were characterized by plate to plate rheometry measuring the storage modulus in situ after mixing hydrogel components and incubating at 37° C. (FIG. 3A). The final pH of the hydrogel precursor solution was modified by dissolving the polymer in solutions with different pHs. AO-PEG solutions at 3 wt % (r=1) at pH 6.5 gelled within 5 minutes. When the pH was raised to 7.2, gelation occurred in 30 min. At a pH of 8.0 hydrogel formation was considerably slowed, and the gel was only partially crosslinked at 30 minutes. The data demonstrate that by controlling the pH, the rate of gelation can be tuned. This result is particularly useful for wound/disease models that require a minimally invasive surgery and biomaterials that form hydrogels.

The amount of water absorbed by the gel and the amount that it is able to swell are important properties of materials for biomedical applications. The water content and swelling ratio of different hydrogel formulations were quantified for the different weight percent gels as well as different r ratios. The water content was quantified by dividing the water weight of the gel by total weight. Increasing the r ratio from 0.7 to 1.0 of 3% PEG hydrogels resulted in a decrease in the water content from 99.26%+/−0.08 to 98.49%+/−0.14 (FIG. 3B). The r ratio also had an effect on the swelling ratio of the gel. The swelling ratio was calculated by dividing swollen gel weight by non-swollen gel weight. As the r ratio increased to 1.0 (moles of aldehyde=moles of aminooxy) for the 3 wt % gels, the swelling ratio decreased from 1.76+/−0.07 to 1.09+/−0.02 (FIG. 3C) indicating that the more tightly the network is crosslinked, the lower water content and swelling ratio. Varying the polymer percentage (3 wt %, 5 wt %, and 7 wt %) with a constant crosslinking ratio (r=1) resulted in decreasing water content from 98.49%+/−0.14 to 95.78%+/−0.25 as the weight percent increased (FIG. 3B). The swelling ratio increased with increasing weight percent from 1.09+/−0.02 to 1.45+/−0.17 (FIG. 3C). Thus, by changing the amount of AO-PEG and the r ratio it is possible to tune to the amount of water absorbed and the swelling ratio.

Hydrogels for Cell Encapsulations

Stem cell encapsulation is a key area of research in the fields of drug delivery, tissue engineering, and regenerative medicine. (Drury, Mooney 2003) Of the available stem cell lineages, mesenechymal stem cells (MSCs) are particular interesting because they are multipotent and offer an autologous treatment approach. (Maumus, Guerit et al. 2011; Motaln, Schichor et al. 2010) MSCs have been differentiated in vitro and in vivo into osteogenic, chondrogenic, and adipogenic lineages, for example, making MSCs an attractive treatment option for degenerative disease and tissue/organ repair. (Maumus, Guerit et al. 2011; Deans, Moseley 2000) For the therapeutic effect of stem cells to be realized it is necessary that the cells be delivered efficiently to the desired location and effectively encapsulated such that the cells stay at the site of delivery. (Drury, Mooney 2003; Kretlow, Klouda et al. 2007).

Two main approaches exist for stem cell delivery/encapsulation: 1) seeding cells onto preformed scaffolds and 2) encapsulating cells during scaffold formation. The former strategy offers access to a wide range of materials and engineering approaches; however, nutrient diffusion and uniform cellular distribution in larger scale constructs can be problematic. The latter approach is advantageous because the cells and scaffold precursors can be mixed prior to scaffold formation allowing for uniform distribution of cells and synthesis of large areas of cell-laden material. This also allows the material and cellular cargo to be injectable and delivered directly to the site of interest.

Encapsulation of MSCs within oxime cross-linked hydrogels functionalized with a RGD adhesion peptide was performed to determine if cells could survive the gelation process, to investigate the potential to use these gels as a three-dimensional gel matrix, and the stability of the oxime bond. Ketone-modified RGD was synthesized following standard solid phase peptide synthesis with the ketone added to the N-terminus using Fmoc-5-aminolevulinic acid (see the above section of Materials and Methods for details). AO-PEG was modified with RGD (PEG-RGD) to achieve a 100 μM final concentration of RGD in the hydrogel. Mouse MSCs (5,000 cells/μL of gel) in complete medium were added to PEG-RGD (in PBS buffer pH=7.4). This mixture was then added to the cross-linker, glutaraldehyde, to result in a 3.0 wt % AO-PEG gel with an r ratio of 0.7. Thus, the hydrogel was able to form in the presence of cells and serum, indicating that it is amenable for rapid hydrogel formation in the presence of a variety of different biological functional groups and living cells.

Live/dead staining of the encapsulated cells at days 1, 4, and 7 post-gelation showed high viability (FIG. 4A-C). Metabolic activity of the encapsulated cells was assessed by MTT assay (FIG. 4H). The relative absorbance by MTT doubled from 1 to 7 days indicating that the cells were metabolicaly active and proliferating. Glutaraldehyde is known as a cell fixative, yet the cells not only survived the crosslinking procedure, they proliferated. We hypothesize that the ability to encapsulate living cells may be due in part to the reactivity of aminooxy groups to form stable oxime bonds in aqueous solution compared to the unstable imines formed by amine groups. (Maynard, Broyer et al. 2009) It is well known that oxime bond formation occurs in the presence of amines. In fact, this reaction has been widely used for site specific modification of proteins (Maynard, Broyer et al. 2009) and to specifically label aldehyde moieties on living cells and tissues. (Baskin, Dehnert et al. 2010) Thus, with the reaction conditions used, it is likely that the glutaraldehyde preferentially reacts with the aminooxy groups of the polymer, leaving the MSCs unharmed. Exclusive reaction with more reactive amines on proteins, leaving other less reactive amines untouched has been reported for glutaraldehyde. (Avrameas, Ternynck 1969).

Figure 7:
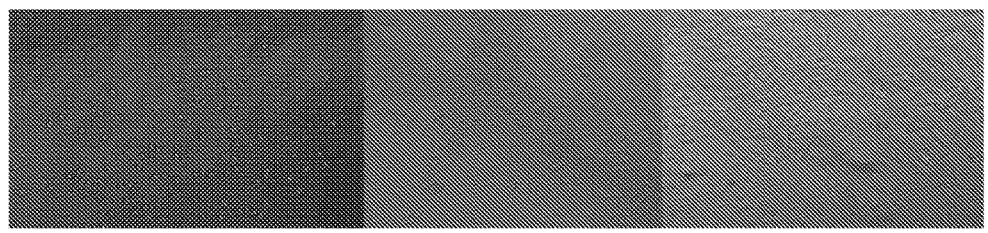
FIG. 7 is a set of images showing MSCs seeded on top of hydrogels from left to right: 1 h, 5 h, 24 h.
Figure 8:
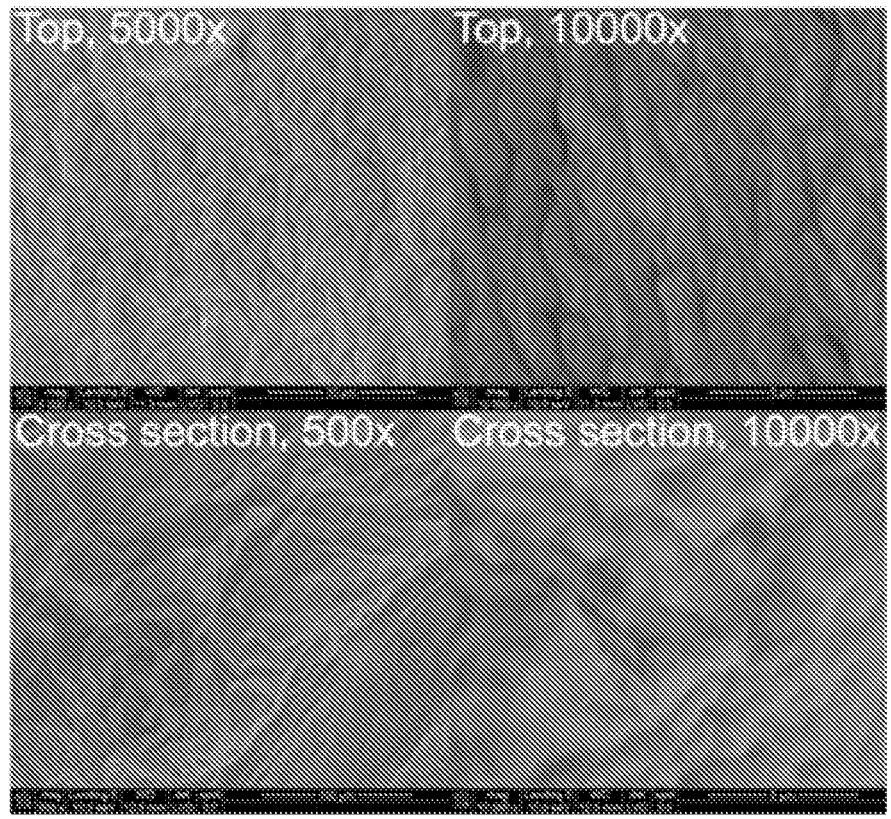
FIG. 8 is a set of images showing SEM images of hydrogels at 250 Pa, 3% PEG r=0.7 gels.

To determine if the cells could remodel the material in the absence of enzymatically degradable crosslinkers, spreading was assessed at 1, 4 and 7-days for cells plated inside the hydrogels. mMSCs (5000 cells/μL) were encapsulated inside RGD (100 μM) functionalized AO-PEG (3 wt %, r=0.7) hydrogels as described above or on top of the hydrogel. Although cells plated on top of the hydrogel exhibited spread morphology over the 7-days of culture (FIG. 4D and FIG. 7), the MSCs encapsulated in an RGD functionalized hydrogel exhibited a rounded morphology over the course of the 7 day experiment (FIG. 4E-G). This result indicates the stability and non-degradability of the oxime bond in the presence of cells and aqueous environment since cells require hydrogel degradation/remodeling to be able to spread. This result also suggests that the hydrogels may be useful for specific degradation of the gel, where a degradable linker for a particular enzyme is introduced into the system. These studies are underway. The SEM imaging looked typical for nano-porous PEG gels and did not show any poors larger than 5 μm in size, which is the resolution of the instrument used (FIG. 4I and FIG. 8).

CONCLUSIONS

In conclusion, a novel methodology has been developed to synthesize biocompatible and biofunctionalized hydrogels that encapsulate stem cells (3-D) or support adherence of the cells (2-D) by oxime bond formation. The mechanical properties, water absorption, and swelling ratio of this system can be tuned by adjusting the weight percent of the aminooxy-PEG and the reactivity ratio of aldehyde to aminooxy. The rate of gelation can easily be tuned by adjusting the pH of the system, within a mild pH range that is still applicable for tissue engineering applications. Facile installation of an integrin binding peptide (RGD) to the matrix was demonstrated.

Mouse MSCs were able to adhere to the gels in 2-D and 3-D. MSCs encapsulated within the oxime cross-linked PEG hydrogel were viable and metabolically active for at least seven days demonstrating the biocompatibility of this approach for cell encapsulation. The material was non-degradable up to seven days, and suggesting that application of an enzymatically degradable cross-linker could facilitate tissue-specific cellular infiltration and spreading throughout the material. The ability to tune the properties and gelation rate of this system as well as encapsulate stem cells will allow this methodology to be applied as a functional coating and injectable material for stem cell therapies in research and clinical settings.

Example 3

Synthesis of PEG-aldehyde 8-armed PEG (MW=20 kDa) was azeotropically distilled in toluene to remove water. To a PEG solution in toluene 3-chloropropionaldehyde was added under Ar at room temperature. Powdered NaOH (240 mg, 6 mmol) was then added, and the resultant suspension was stirred vigorously under reflux for 48 h. After cooling to room temperature, the suspension was filtered, and the filtrate was dried under vacuum. The residue was further purified by dialysis against water:methanol mixtures and then freeze dried to obtain the product as a white powder.

Scheme 4. Method for producing PEG-aldehyde having protecting groups.

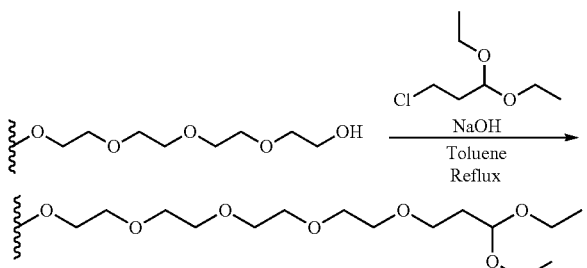

Scheme 5. Method for producing PEG-aldehyde.

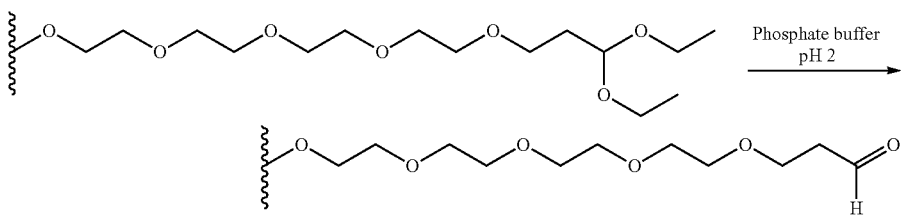

REFERENCES (1) Christman, K. L.; Lee, R. J. *J Am. Coll. Cardiol.* 2006, 48, 907-913.
(2) Wang, H. B.; Zhou, J.; Liu, Z. Q.; Wang, C. Y. *J. Cell. Molec. Med.* 2010, 14, 1044-1055.
(3) Yu, L.; Ding, J. D. *Chem. Soc. Rev.* 2008, 37, 1473-1481.
(4) Fisher, O. Z.; Khademhosseini, A.; Langer, R.; Peppas, N. A. *Acc. Chem. Res.* 2010, 43, 419-428.
(5) Eisenbarth, E. *Adv. Eng. Mater.* 2007, 9, 1051-1060.
(6) Lutolf, M. P.; Hubbell, J. A. *Nat Biotechnol.* 2005, 23, 47-55.
(7) Nimmo, C. M.; Shoichet, M. S. *Bioconjug Chem* 2011, 22, 2199-2209.
(8) Liu, S. Q.; Tian, Q. A.; Wang, L.; Hedrick, J. L.; Hui, J. H. P.; Yang, Y. Y.; Ee, P. L. R. *Macromol. Rapid Comm.* 2010, 31, 1148-1154.
(9) Patterson, J.; Hubbell, J. A. *Biomaterials* 2010, 31, 7836-7845.
(10) Yang, T.; Long, H.; Malkoch, M.; Gamstedt, E. K.; Berglund, L.; Hult, A. *J. Polym. Sci. Poly. Chem.* 2011, 49, 4044-4054.
11) Fairbanks, B. D.; Schwartz, M. P.; Halevi, A. E.; Nuttelman, C. R.; Bowman, C. N.; Anseth, K. S. *Adv. Mater.* 2009, 21, 5005-+.
(12) Yang, J. Y.; Jacobsen, M. T.; Pan, H. Z.; Kopecek, J. *Macromol. Biosci.* 2010, 10, 445-454.
(13) DeForest, C. A.; Anseth, K. S. *Nature Chem.* 2011, 3, 925-931.
(14) Kalia, J.; Raines, R. T. *Angew. Chem. Int. Ed.* 2008, 47, 7523-7526.
(15) Christman, K. L.; Broyer, R. M.; Schopf, E.; Kolodziej, C. M.; Chen, Y.; Maynard, H. D. *Langmuir* 2011, 27, 1415-1418.
(16) Heredia, K. L.; Tolstyka, Z. P.; Maynard, H. D. *Macromolecules* 2007, 40, 4772-4779.
(17) Zeng, Y.; Ramya, T. N. C.; Dirksen, A.; Dawson, P. E.; Paulson, J. C. *Nature Meth.* 2009, 6, 207-209.
(18) Baskin, J. M.; Dehnert, K. W.; Laughlin, S. T.; Amacher, S. L.; Bertozzi, C. R. *PNAS* 2010, 107, 10360-10365.
(19) Mimeault, M.; Hauke, R.; Batra, S. K. *Clin. Pharmacol. Ther.* 2007, 82, 252-264.
(20) Yang, Z. G.; Ding, J. D. *Macromol. Rapid Comm.* 2008, 29, 751-756.
(21) Zhu, J. M. *Biomaterials* 2010, 31, 4639-4656.
(22) Christman, K. L.; Schopf, E.; Broyer, R. M.; Li, R. C.; Chen, Y.; Maynard, H. D. *J. Am. Chem. Soc.* 2009, 131, 521-527.
(23) Migneault, I.; Dartiguenave, C.; Bertrand, M. J.; Waldron, K. C. *BioTechniques* 2004, 37, 790-802.
(24) Drury, J. L.; Mooney, D. J. *Biomaterials* 2003, 24, 4337-4351.
(25) Maumus, M.; Guerit, D.; Toupet, K.; Jorgensen, C.; Noel, D. *Stem Cell Res. Ther.* 2011, 2.
(26) Motaln, H.; Schichor, C.; Lah, T. T. *Cancer* 2010, 116, 2519-2530.
(27) Deans, R. J.; Moseley, A. B. *Exper. Hematol.* 2000, 28, 875-884.
(28) Kretlow, J. D.; Klouda, L.; Mikos, A. G. *Adv. Drug Deliver. Rev.* 2007, 59, 263-273.
(29) Maynard, H. D.; Broyer, R. M.; Kolodziej, C. M. In *Click Chemistry for Biotechnology and Materials Science*; Lahann, J., Ed.; Wiley, Inc.: West Sussex, UK, 2009, p 53-68.
(30) Avrameas, S.; Ternynck, T. *Immunochemistry* 1969, 6, 53-66.
(31) Mischa Zelzer, Simon J. Todd, Andrew R. Hirst, Tom O. McDonalde and Rein V. Ulijn *Biomater. Sci.*, 2013, 1, 11-39.
(32) Gregory N. Grover, Jonathan Lam, Thi H. Nguyen, Tatiana Segura, and Heather D. Maynard *Biomacromolecules*, 2012, 13 (10), pp 3013-3017.

(33) Lutolf M P & Hubbell J A Synthesis and physicochemical characterization of end-linked poly(ethylene glycol)-co-peptide hydrogels formed by Michael-type addition, Biomacromolecules, 2003, 4(3):713-722.

We claim:

1. A method of creating a hydrogel, comprising the step of condensing first and second functional groups, wherein the first group comprises a molecule or macromolecule of interest containing two or more hydroxylamine or aminooxy groups and the second group comprises a molecule or macromolecule of interest containing two or more aldehyde, ketone, or other reactive oxo groups, under conditions such that a hydrogel forms, wherein at least one of the molecules or macromolecules of interest is a polyethylene glycol-based molecule or macromolecule and the molecules or macromolecules of interest are alkyl-or alkoxy-based molecules with two or more hydroxylamine or aminooxy groups or with two or more aldehyde, ketone, or other reactive oxo groups, wherein oxime bonds of the hydrogel are non-degradable for up to seven days under physiological conditions.

2. The method according to claim 1, wherein the molecules or macromolecules of interest are selected from the group consisting of polyethylene glycol, polyethylene glycol (PEG) derivative, polystyrene sulfonate, poly(styrene sulfonate-co-polyethylene glycol methacrylate), polypropylene oxide, polyethylene oxide, and poly(styrene sulfonate-co-polyethylene glycol acrylate).

3. The method according to claim 1, wherein the conditions for the hydrogel formation comprises at room temperature, in aqueous solutions and under pH=6-7.4.

4. The method according to claim 1, wherein the molecule or macromolecule of interest further comprises bio-degradable bonds.

5. The method according to claim 1, wherein the molecule or macromolecule of interest in the first group is a polyethylene glycol (PEG) derivative.

6. The method according to claim 5, wherein the PEG derivative comprises two or more groups of $NH_2$—O—$CH_2CH_2O)_n$—, wherein n =1- 1000.

7. The method according to claim 1, wherein the molecule or macromolecule of interest in the second group comprises two or more groups of $R_1CO$-L-$COR_2$, wherein $R_1$ and $R_2$ are independently selected from the group consisting of H, Cl, Br, I, -Alkyl, -Alkenyl, -Alkynyl, -Aryl, -Heteroaryl, -Heterocyclyl, OR3, SR4, NR5, and biomolecules and L is a linker molecule, and wherein $R_3$, $R_4$ and $R_5$ are independently selected from the group consisting of H, Cl, Br, I, -Alkyl, -Alkenyl, -Alkynyl, -Aryl, -Heteroaryl and -Heterocyclyl.

8. The method according to claim 7, wherein L is selected from the group consisting of -Alkyl-, -Alkenyl-, Alkynyl-, -Aryl-, -Heteroaryl-, -Heterocyclyl-, and -$(CH_2CH_2O)n$—, wherein n =0-1000.

9. The method according to claim 8, wherein the biomolecules are selected from the group consisting of proteins, enzymes, antibodies, peptides, and nucleic acids.

10. The method of claim 9 wherein the nucleic acid is selected from the group consisting of DNA, RNA, siRNA, antisense RNA, RNAi, snRNA, miRNA, and cDNA.

11. The method according to claim 1, wherein the molecule or macromolecule of interest in the first and second group is a polyethylene glycol (PEG) derivative.

12. The method according to claim 11, wherein the polyethylene glycol (PEG) derivative comprises two or more groups of $R_6CO$—$(CH_2)_m$—COO—$(CH_2CH_2O)_n$—, where $R_6$ is selected from the group consisting of H, Cl, Br, I, -Alkyl, -Alkenyl, -Alkynyl, -Aryl, -Heteroaryl, - Heterocyclyl, -OR3, -SR4, -NR5, and biomolecules and wherein m=1-1000 and n =0-1000, wherein $R_3$, $R_4$ and $R_5$ are independently selected from the group consisting of H, Cl, Br, I, -Alkyl, -Alkenyl, -Alkynyl, -Aryl, -Heteroaryl and -Heterocyclyl.

13. The method according to claim 12, wherein m=1-20.

14. The method according to claim 12, wherein the biomolecule is selected from the group consisting of proteins, enzymes, antibodies, peptides, and nucleic acids.

15. The method of claim 14 wherein the nucleic acid is selected from the group consisting of DNA, RNA, RNAi, antisense RNA, snRNA, miRNA, siRNA, and cDNA.

16. The method according to claim 11, wherein the polyethylene glycol (PEG) derivative comprises two or more groups of HCO—$(CH_2)_m$—O—$(CH_2CH_2O)n$—, wherein m =1-1000and wherein n =0-1000.

17. The method according to claim 16, wherein m =1-20.

18. A method of creating a hydrogel, comprising the step of condensing functional groups, wherein the functional groups comprise a molecule or macromolecule of interest containing two or more hydroxylamine or aminooxy groups and two or more aldehyde, ketone, or other reactive oxo groups, under conditions such that a hydrogel forms, wherein at least one of the molecules or macromolecules of interest is a polyethylene glycol-based molecule or macromolecule and the molecules or macromolecules of interest are alkyl- or alkoxy-based molecules with two or more hydroxylamine or aminooxy groups or with two or more aldehyde, ketone, or other reactive oxo groups, wherein oxime bonds of the hydrogel are non-degradable for up to seven days under physiological conditions.

19. A hydrogel formed by the method of claim 1.

20. The hydrogel according to claim 19, wherein the hydrogel is bio-degradable.

21. The hydrogel according to claim 19, wherein the hydrogel is bio-compatible.

22. A hydrogel comprising a condensation product wherein the condensation product forms from condensing first and second functional groups, and wherein the first group comprises a molecule or macromolecule of interest containing two or more hydroxylamine or aminooxy groups and the second group comprises a molecule or macromolecule of interest containing two or more aldehyde, ketone, or other reactive oxo groups, wherein at least one of the molecules or macromolecules of interest is a polyethylene glycol-based molecule or macromolecule and the molecules or macromolecules of interest are alkyl- or alkoxy-based molecules with two or more hydroxylamine or aminooxy groups or with two or more aldehyde, ketone, or other reactive oxo groups, wherein oxime bonds of the hydrogel are non-degradable for up to seven days under physiological conditions.

* * * * *